(12) United States Patent
Hu et al.

(10) Patent No.: US 10,524,458 B2
(45) Date of Patent: *Jan. 7, 2020

(54) HUMANIZED C3 ANIMALS

(71) Applicant: REGENERON PHARMACEUTICALS, INC., Tarrytown, NY (US)

(72) Inventors: Ying Hu, Scarsdale, NY (US); Adrianna Latuszek, Sleepy Hollow, NY (US); Jingtai Cao, White Plains, NY (US); Alexander Mujica, Elmsford, NY (US); Stanley Wiegand, Hopewell Junction, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,377

(22) Filed: Jul. 2, 2018

(65) Prior Publication Data

US 2018/0332833 A1    Nov. 22, 2018

Related U.S. Application Data

(60) Continuation of application No. 15/660,833, filed on Jul. 26, 2017, which is a division of application No. 14/703,818, filed on May 4, 2015, now Pat. No. 9,795,121.

(60) Provisional application No. 62/067,836, filed on Oct. 23, 2014, provisional application No. 61/988,581, filed on May 5, 2014.

(51) Int. Cl.
*A01K 67/027* (2006.01)
*A61K 49/00* (2006.01)
*C07K 14/47* (2006.01)

(52) U.S. Cl.
CPC ...... *A01K 67/0278* (2013.01); *A61K 49/0008* (2013.01); *A01K 2207/15* (2013.01); *A01K 2217/072* (2013.01); *A01K 2227/105* (2013.01); *A01K 2267/03* (2013.01); *A01K 2267/0368* (2013.01); *C07K 14/472* (2013.01)

(58) Field of Classification Search
CPC .................................................. A01K 67/0278
See application file for complete search history.

(56) References Cited

U.S. PATENT DOCUMENTS

| | | |
|---|---|---|
| 4,708,871 A | 11/1987 | Geysen |
| 4,833,092 A | 5/1989 | Geysen |
| 5,223,409 A | 6/1993 | Ladner et al. |
| 5,403,484 A | 4/1995 | Ladner et al. |
| 5,427,908 A | 6/1995 | Dower et al. |
| 5,432,018 A | 7/1995 | Dower et al. |
| 5,498,530 A | 3/1996 | Schatz et al. |
| 5,556,762 A | 9/1996 | Pinilla et al. |
| 5,571,689 A | 11/1996 | Heuckeroth et al. |
| 5,580,717 A | 12/1996 | Dower et al. |
| 5,624,821 A | 4/1997 | Winter et al. |
| 5,644,048 A | 7/1997 | Yau |
| 5,648,260 A | 7/1997 | Winter et al. |
| 5,663,143 A | 9/1997 | Ley et al. |
| 5,698,426 A | 12/1997 | Huse |
| 5,723,286 A | 3/1998 | Dower et al. |
| 5,723,323 A | 3/1998 | Kauffman et al. |

(Continued)

FOREIGN PATENT DOCUMENTS

| | | |
|---|---|---|
| CN | 1278299 A | 12/2000 |
| CN | 101970494 A | 2/2011 |

(Continued)

OTHER PUBLICATIONS

Ding et al. (Investigative Ophthalmology & Visual Science Apr. 2011, vol. 52, 958. ARVO Annual Meeting Abstract. Apr. 2011. Development and Characterization of Humanized Complement Factor H (CFH) Transgenic Mice), (Year: 2011).*

(Continued)

*Primary Examiner* — Scott Long

(74) *Attorney, Agent, or Firm* — Scully, Scott, Murphy & Presser, P.C.; Eileen Woo

(57) ABSTRACT

Non-human animals comprising a human or humanized C3 and/or C5 nucleic acid sequence are provided as well as methods for using the same to identify compounds capable of modulating the complement system. Non-human animals that comprise a replacement of the endogenous C5 gene and/or C3 gene with a human or humanized C5 gene and/or C3 gene, and methods for making and using the non-human animals, are described. Non-human animals comprising a human or humanized C5 gene under control of non-human C5 regulatory elements is also provided, including non-human animals that have a replacement of non-human C5-encoding sequence with human C5-encoding sequence at an endogenous non-human C5 locus. Non-human animals comprising a human or humanized C3 gene under control of non-human C3 regulatory elements is also provided, including non-human animals that have a replacement of non-human C3 protein-encoding sequence with human or humanized C3 protein-encoding sequence at an endogenous non-human C3 locus. Non-human animals comprising human or humanized C3 and/or C5 sequences, wherein the non-human animals are rodents, e.g., mice or rats, are provided.

24 Claims, 19 Drawing Sheets

Specification includes a Sequence Listing.

(56) References Cited

U.S. PATENT DOCUMENTS

| | | | |
|---|---|---|---|
| 5,734,018 | A | 3/1998 | Rutter et al. |
| 5,750,373 | A | 5/1998 | Garrard et al. |
| 5,763,192 | A | 6/1998 | Kauffman et al. |
| 5,770,434 | A | 6/1998 | Huse |
| 6,355,245 | B1 | 3/2002 | Evans et al. |
| 6,656,687 | B1 | 12/2003 | Hyldig-Nielsen |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 9,795,121 | B2 * | 10/2017 | Hu ..................... A61K 49/0008 |
| 2005/0260198 | A1 | 11/2005 | Holers et al. |
| 2009/0032592 | A1 | 2/2009 | Christensen |
| 2015/0313194 | A1 | 11/2015 | Hu et al. |
| 2017/0332611 | A1 | 11/2017 | Hu et al. |

FOREIGN PATENT DOCUMENTS

| | | |
|---|---|---|
| EP | 1 701 611 B1 | 9/2006 |
| WO | 84/03506 A1 | 9/1984 |
| WO | 84/03564 A1 | 9/1984 |
| WO | 94/29351 A2 | 12/1994 |
| WO | 97/15390 A1 | 5/1997 |
| WO | 99/51642 A1 | 10/1999 |
| WO | 00/00823 A1 | 1/2000 |
| WO | 00/39585 A1 | 7/2000 |
| WO | 2005/060739 A1 | 7/2005 |
| WO | 2013/192030 A1 | 12/2013 |
| WO | 2015/171523 A1 | 11/2015 |

OTHER PUBLICATIONS

Jin-Dong Ding et al. Chapter 28 The Role of Complement Dysregulation in AMD Mouse Models; J. D. Ash et al. (eds.), Retinal Degenerative Diseases, Advances in Experimental Medicine and Biology 801, DOI 10.1007/978-1-4614-3209-8_28, © Springer Science+Business Media, LLC 2014) (Year: 2014).*

Chinese Office Action and Search Report dated Feb. 3, 2019 received in Chinese Application No. 201580034127.8, together with an English-language translation.

Valenzuela D.M. et al., "High-Throughput Engineering of the Mouse Genome Coupled With High-Resolution Expression Analysis", *Nature Biotechnology* 21(6):652-659 (Jun. 2003).

Van Der Putten H. et al., "Efficient Insertion of Genes into the Mouse Germ Line Via Retroviral Vectors," *Proc. Natl. Acad. Sci. USA* 82:6148-6152 (Sep. 1985).

Vik D.P. et al., "Structural Features of the Human C3 Gene: Intron/Exon Organization, Transcriptional Start Site, and Promoter Region Sequence", *Biochemistry* 30(4):1080-1085 (1991).

Wahlestedt C. et al., "Potent and Nontoxic Antisense Oligonucleotides Containing Locked Nucleic Acids", *PNAS* 97(10):5633-5638 (May 9, 2000).

Wetsel R.A. et al,, "Deficiency of the Murine Fifth Complement Component (C5)", *The Journal of Biological Chemistry* 265(5):2435-2440 (Feb. 15, 1990).

International Search Report dated Aug. 28, 2015 received in International Application No. PCT/US2015/029111.

Written Opinion of the International Search Authority dated Aug. 28, 2015 received in International Application No. PCT/US2015/029111.

European Examination Report dated Feb. 14, 2018 received in European Patent Application No. 15 722 639.0.

Ailenberg M. et al., "Establishment and Chimera Analysis of 129/SvEv- and C57BL/6-Derived Mouse Embryonic Stem Cell Lines", BioTechniques 29(5):1024-1032 (Nov. 2000).

Austen Jr. W.G. et al, "The Role of Complement and Natural Antibody in Intestinal Ischemia-Reperfusion Injury", International Journal of Immunopathology and Pharmacology 16(1):1-8 (2003).

Beaucage S.L., "Oligodeoxyribonucleotides Synthesis: Phosphoramidite Approach", Chapter 3 in Methods in Molecular Biology 20:33-61 (1993).

Capaldi D.C. et al, "Highly Efficient Solid Phase Synthesis of Oligonucleotide Analogs Containing Phosphorodithioate Linkages", Nucleic Acids Research 28(9):e40 (2000).

Chang B. et al, "Age-Related Retinal Degeneration (arrd2) in a Novel Mouse Model Due to a Nonsense Mutation in the Mdm1 Gene", Human Molecular Genetics 117(24):3929-3941 (2008).

Clackson T. et al., "Making Antibody Fragments Using Phage Display Libraries", Nature 352:624-628 (Aug. 15, 1991).

Copland D.A. et al., "Systemic and Local Anti-C5 Therapy Reduces the Disease Severity in Experimental Autoimmune Uveoretinitis", Clinical and Experimental Immunology 159:303-314 (2009).

Cousins S.W. et al., "The Role of Aging, High Fat Diet and Blue Light Exposure in an Experimental Mouse Model for Basal Laminar Deposit Formation", Exp. Eye Res. 75:543-553 (2002).

Ding J-D et al., "The Role of Complement Dysregulation in AMD Mouse Models", Chapter 28, J.D. Ash et al. (eds.) Retinal Degenerative Diseases, Advances in Experimental Medicine and Biology 801:213-219 (2014).

Ding J. et al., "Development and Characterization of Humanized Complement Factor H (CFH) Transgenic Mice", ARVC Annual Meeting Abstract, Investigative Ophthalmology & Visual Science 52:958 (Apr. 2011).

Dithmar S. et al., "Ultrastructural Changes in Bruch's Membrane of Apolipoprotein E-Deficient Mice", Investigative Ophthalmology & Visual Science 41(8):2035-2042 (Jul. 2000).

Doyle S.L et al, "NLRP3 Has a Protective Role in Age-Related Macular Degeneration Through the Induction of IL-18 by Drusen Components", Nat Med. 18(5):791-798 (May 2012).

Drouin S.M. et al., "Cutting Edge: The Absence of C3 Demonstrates a Role for Complement in Th2 Effector Functions in a Murine Model of Pulmonary Allergy", The Journal of Immunology 167:4141-4145 (2001).

Drouin S.M. et al, "A Protective Role for the Fifth Complement Component (C5) in Allergic Airway Disease", Am Respir Crit Care Med 173:852-857 (2006).

Duncan A.R. et al., "The Binding Site for C1q on IgG", Nature 332:738-740 (Apr. 21, 1988).

Egholm M. et al., "PNA Hybridizes to Complementary Oligonucleotides Obeying the Watson-Crick Hydrogen-Bonding Roles", Nature 365:566-568 (Oct. 7, 1993).

Espinosa-Heidmann D.G. et al., "Cigarette Smoke-Related Oxidants and the Dvelopment of Sub-RPE Deposits in an Experimental Animal Model of Dry AMD", Investigative Ophthalmology & Visual Science 47(2):729-737 (Feb. 2006).

Flierl M.A. et al., "Functions of the Complement Components C3 and C5 During Sepsis", The FASEB Journal 22:3483-3490 (2008).

Geysen H.M. et al., "Use of Peptide Synthesis to Probe Viral Antigens for Epitopes to a Resolution of a Single Amino Acid", Proc. Natl. Acad. Sci. USA 81:3998-4002 (Jul. 1984).

Geysen H.M. et al., "Small Peptides Induce Antibodies With a Sequence and Structural Requirement for Binding Antigen Comparable to Antibodies Raised Against the Native Protein", Proc. Natl. Acad. Sci. USA 82:178-182 (Jan. 1985).

Geysen H.M. et al, "Strategies for Epitope Analysis Using Peptide Synthesis", Journal of Immunological Methods 102:259-274 (1987).

Giclas P.C., "Classical Pathway Evaluation", Current Protocols in Immunology Unit 13.1, CPI Supplement 9, (26 pages) (2001).

Guo R-F et al., "Role of C5A in Inflammatory Responses", Annu. Rev. Immunol. 23:821-852 (2005).

Hollyfield J.G., "Age-Related Macular Degeneration: The Molecular Link Between Oxidative Damage, Tissue-Specific Inflammation and Outer Retinal Disease, The Proctor Lecture", Investigative Ophthalmology & Visual Science 51(3):1276-1281 (Mar. 2010).

Holt D.S. et al., "Targeted Deletion of the CD59 Gene Causes Spontaneous Intravascular Hemolysis and Hemoglobinuria", Blood 98(2):442-449 (Jul. 15, 2001).

Hyrup B. et al., "Peptide Nucleic Acids (PNA): Synthesis, Properties and Potential Applications", Bioorganic & Medicinal Chemistry 4(1):5-23 (1996).

Imamura Y. et al., "Drusen, Choroidal Neovascularization, and Retinal Pigment Epithelium Dysfunction in SOD1-Deficient Mice: A Model of Age-Related Macular Degeneration", PNAS 103(30):11282-11287 (Jul. 25, 2006).

(56) References Cited

OTHER PUBLICATIONS

Jähner D. et al., "Insertion of the Bacterial Gpt Gene into the Germ Line of Mice by Retroviral Infection", Proc. Natl. Acad. Sci. USA 82:6927-6931 (Oct. 1985).
Jaenisch R., "Germ Line Integration and Mendelian Transmission of the Exogenous Moloney Leukemia Virus", Proc. Nat. Acad. Sci. USA 73(4):1260-1264 (Apr. 1976).
Kaneko H. et al., "DICER1 Deficit Induces Alu RNA Toxicity in Age-Related Macular Degeneration", Nature 471 (7338)325-330 (Mar. 17, 2011).
Kang A.S. et al., "Linkage of Recognition and Replication Functions by Assembling Combinatorial Antibody Fab Libraries Along Phase Surfaces", Proc. Natl. Acad. Sci. USA 88:4363-4366 (May 1991).
Kuehn M.H. et al., "Retinal Synthesis and Deposition of Complement Components Induced by Ocular Hypertension", Experimental Eye Research 83:620-628 (2006).
Lambert V. et al., "Laser-Induced Choroidal Neovascularization Model to Study Age-Related Macular Degeneration in Mice", Nature Protocols 8(11):2197-2211 (2013).
Latusek A. et al., "Evaluation of Complement Activity in Wild Type, C5 Knockout and Humanized Mice for Drug Discovery", Investigative Ophthalmology & Visual Science 55(1324), Meeting Abstract, 1 page (Apr. 2014).
Mag M. et al., "Synthesis and Selective Cleavage of an Oligodeoxynucleotide Containing a Bridged Internucleotide 5'-Phosphorothioate Linkage", Nucleic Acids Research 19(7):1437-1441 (1991).
Makrides S.C., "Therapeutic Inhibition of the Complement System", Pharmacological Reviews 50(1):59-87 (1998).
McKay R.A. et al., "Characterization of a Potent and Specific Class of Antisense Oligonucleotide Inhibitor of Human Protein Kinase C-a Expression", The Journal of Biological Chemistry 274(3):1715-1722 (Jan. 15, 1999).
Mollnes T.E. et al., "Strategies of Therapeutic Complement Inhibition", Molecular Immunology 43:107-121 (2006).
Mullins R.F. et al., "Drusen Associated With Aging and Age-Related Macular Degeneration Contain Proteins Common to Extracellular Deposits Associated With Atherosclerosis, Elastosis, Amyloidosis, and Dense Deposit Disease", FASEB J. 14:835-846 (2000).
Murphy A.J. et al., "Mice With Megabase Humanization of Their Immunoglobulin Genes Generate Antibodies as Efficiently as Normal Mice", PNAS 111(14):5153-5158 (Apr. 8, 2014).
Needels M.C. et al., "Generation and Screening of an Oligonucleotide-Encoded Synthetic Peptide Library", Proc. Natl. Acad. Sci. USA 90:10700-10704 (Nov. 1993).
Nielsen P.E. et al., "Peptide Nucleic Acids (PNAs): Potential Anti-Sense and Anti-Gene Agents", Anti-Cancer Drug Design 8:53-63 (1993).
Ohlsson M. et al., "Complement Activation Following Optic Nerve Crush in the Adult Rat", Journal of Neurotrauma 20(9):895-904 (2003).
Poueymirou W.T. et al., "FO Generation Mice Fully Derived from Gene-Targeted Embryonic Stem Cells Allowing Immediate Phenotypic Analyses", Nature Biotechnology 25(1):91-99 (Jan. 2007).
Rathinam C. et al, "Efficient Differentiation and Function of Human Macrophages in Humanized CSF-1 Mice", Blood 118(11):3119-3128 (2011).
Rudolf M. et al., "Increased Expression of Vascular Endothelial Growth Factor Associated With Accumulation of Lipids in Bruch's Membrane of LDL Receptor Knockout Mice", Br. J. Ophthalmol. 89:1627-1630 (2005.
Smith G.P., "Surface Presentation of Protein Epitopies Using Bacteriophage Expression Systems", Current Opinion in Biotechnology 2:668-673 (1991).
Summerton J., "Morpholino Antisense Oligomers: The Case for an RNase H-Independent Structural Type", Biochimica et Biophysica Acta 1489:141-158 (1999).
Tamamis P. et al., "Design of a Modified Mouse Protein With Ligand Binding Properties of its Human Analog by Molecular Dynamics Simulations: The Case of C3 Inhibition by Compstatin", Proteins 79(11):3166-3179 (Nov. 2011).
Ufret-Vincenty R.L. et al., "Transgenic Mice Expressing Variants of Complement Factor H Develop AMD-Like Retinal Findings", Investigative Ophthalmology & Visual Science 51(11):5878-5887 (Nov. 2010).
Carney D.F. et al., "Structural Aspects of the Human C5 Gene", The Journal of Biological Chemistry 266 (28)18786-18791 (Oct. 5, 1991).
Haviland D.L. et al., "Structure of the Murine Fifth Complement Component (C5) Gene", The Journal of Biological Chemistry 266(18):11818-11825 (Jun. 25, 1991).
Wiebauer K. et al., "Isolation and Analysis of Genomic DNA Clones Encoding the Third Component of Mouse Complement", Proc. Natl. Acad. Sci. USA 79:7077-7081 (Dec. 1982).
Japanese Notice of Reasons for Rejection dated May 10, 2019 received in Japanese Patent Application No. 2016-566228, together with an English-language translation.
Glick B. et al., Moleculyarnaya Biotehnologiya. Printsipy i primeneniye. Moscow: Mir, 2002, pp. 45-47, together with an English-language translation.
Russian Office Action dated Jul. 30, 2019 received in Russian Patent Application No. 2016146390, together with an English-language translation.

\* cited by examiner

HUMANIZED C3 ANIMALS

CROSS-REFERENCE TO RELATED APPLICATIONS

This application is a continuation of U.S. patent application Ser. No. 15/660,833, filed Jul. 26, 2017, which is a divisional of U.S. patent application Ser. No. 14/703,818, filed May 4, 2015, now U.S. Pat. No. 9,795,121, which claims priority to U.S. Provisional Patent Application No. 62/067,836, filed Oct. 23, 2014 and U.S. Provisional Patent Application No. 61/988,581, filed May 5, 2014, the disclosures of each of which are incorporated by reference herein in their entirety.

INCORPORATION BY REFERENCE OF SEQUENCE LISTING

The Sequence Listing is an ASCII text file, named T0031US03_35471AZ_SequenceListing.txt of 10 KB, created on Jun. 29, 2018 and submitted to the United States Patent and Trademark Office via EFS-Web, is incorporated herein by reference.

FIELD OF INVENTION

Disclosed herein are non-human animals comprising nucleic acid sequences encoding a C3 protein and/or a C5 protein that comprise a human sequence as well as transgenic non-human animals comprising a C3 and/or a C5 gene that is human in whole or in part. Also disclosed herein are non-human animals that express human or humanized C3 and/or C5 proteins and methods for using non-human animals comprising human or humanized C3 and/or C5 nucleic acid sequences.

BACKGROUND

Complement proteins C5 and C3 are therapeutic targets for treatment of a variety of human diseases, disorders and conditions that are associated with complement activation, for example, ocular inflammatory and retinal degenerative diseases. The evaluation of pharmacokinetics (PK) and pharmacodynamics (PD) of therapeutic molecules that specifically target human C5 or human C3 proteins are routinely performed in non-human animals, e.g., rodents, e.g., mice or rats. However, the PD of such therapeutic molecules cannot properly be determined in certain non-human animals because these therapeutic molecules do not target the endogenous C5 or C3 proteins.

Moreover, the evaluation of therapeutic efficacy of human-specific C5 or C3 protein antagonists various non-human animal models of diseases associated with an activated complement system is problematic in non-human animals in which such species-specific antagonists do not interact with the endogenous C5 or C3 proteins.

Accordingly, there is a need for non-human animals, e.g., rodents, e.g., murine animals, e.g., mice or rats, in which the C5 and/or C3 genes of the non-human animal are humanized in whole or in part or replaced (e.g., at the endogenous non-human loci) with human C5 and/or C3 genes comprising sequences encoding human or humanized C5 and/or C3 proteins, respectively. There is a need for such humanized non-human animals that express human or humanized C5 and/or C3 proteins in serum at concentrations similar to that of C5 and/or C3 proteins, respectively, present in serum of an age-matched non-human animal, that expresses functional C5 and/or C3 proteins, but does not comprise the human or humanized C5 and/or C3 genes, respectively.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

Non-human animals comprising nucleic acid sequences encoding a C3 and/or a C5 that comprise a human sequence are provided.

Transgenic non-human animals comprising a C3 and/or a C5 gene that is human in whole or in part are provided.

Non-human animals that express human or humanized C3 and/or C5 proteins are provided.

Non-human animals having a replacement (in whole or in part) of endogenous non-human animal C5 and/or C3 genes are provided.

Non-human animals comprising a C5 and/or C3 humanization (in whole or in part) at an endogenous non-human C5 and/or C3 locus are provided.

Non-human animals are provided that have human or humanized C5 and/or C3 genes, wherein the non-human animals do not express endogenous C5 and/or C3 protein, and express human or humanized C5 and/or C3 protein, in serum at concentrations similar to that of C5 and/or C3 proteins, respectively, present in serum of an age-matched non-human animal that expresses functional endogenous C5 and/or C3 proteins, but does not comprise the replacement.

In one aspect, non-human animals comprising a human or humanized C3 and/or C5 nucleic acid sequence are provided.

In one aspect, genetically modified non-human animals are provided that comprise a replacement at an endogenous C5 and/or C3 locus of a gene encoding an endogenous C5 and/or C3 gene encoding a human or humanized C5 and/or C3 protein. Rodents, e.g., mice or rats, are provided that comprise a replacement of an endogenous C5 gene, at an endogenous rodent C5 locus, with a human C5 gene, and/or comprise a replacement of an endogenous C3 gene, at an endogenous rodent C3 locus, with a human C3 gene. In one embodiment, the rodent is a mouse. In one embodiment, the rodent is a rat.

In one aspect, genetically modified rodents, e.g., mice or rats, are provided comprising a replacement at an endogenous rodent C5 locus of a rodent gene encoding C5 protein with a human C5 gene encoding human or humanized C5 protein, wherein expression of the human C5 gene encoding human or humanized C5 protein is under control of rodent regulatory elements at the endogenous rodent C5 locus. In one embodiment, the rodent is a mouse. In one embodiment, the rodent is a rat.

In one embodiment, the human C5 gene encoding human or humanized C5 protein comprises exon 2 through exon 41 of the human C5 gene.

In one embodiment, the rodent is a mouse that is incapable of expressing a mouse C5 protein.

In one embodiment, the rodent is a mouse that expresses a mouse C3 protein encoded by an endogenous mouse C3 gene.

In one embodiment, the rodent is mouse that expresses a human or humanized C3 protein.

In one embodiment, the rodent is a mouse that comprises a replacement at an endogenous mouse C3 locus of a mouse gene encoding C3 protein with a human C3 gene encoding a human or humanized C3 protein.

In one embodiment, expression of the human C3 gene encoding the human or humanized C3 protein is under control of mouse regulatory elements at the endogenous mouse C3 locus.

In one aspect, genetically modified rodents, e.g., mice or rats, are provided comprising a replacement at an endogenous rodent C3 locus of a rodent gene encoding C3 protein with a human C3 gene encoding human or humanized C3 protein, wherein expression of the human C3 gene encoding human or humanized C3 protein is under control of rodent regulatory elements at the endogenous rodent C3 locus. In one embodiment, the rodent is a mouse. In one embodiment, the rodent is a rat.

In one embodiment, the human C3 gene encoding human or humanized C3 protein comprises exon 1 through exon 41 of the human C3 gene.

In one embodiment, the human C3 gene encoding human or humanized C3 protein comprises exon 2 through exon 41 of the human C3 gene.

In one embodiment, the rodent is a mouse that is incapable of expressing a mouse C3 protein.

In one embodiment, the rodent is a mouse that expresses a mouse C5 protein encoded by an endogenous mouse C5 gene.

In one embodiment, the rodent is mouse that expresses a human or humanized C5 protein.

In one embodiment, the rodent is a mouse that comprises a replacement at an endogenous mouse C5 locus of a mouse gene encoding C5 protein with a human C5 gene encoding a human or humanized C5 protein.

In one embodiment, expression of the human C5 gene encoding the human or humanized C5 protein is under control of mouse regulatory elements at the endogenous mouse C5 locus.

In one aspect, genetically modified rodents, e.g., a mouse or rat, are provided that express a human or humanized C5 protein, wherein the rodent that expresses a human or humanized C5 protein comprises a normal complement system, e.g., the levels of complement proteins in the blood, plasma or serum of the rodent expressing human or humanized C5 protein are similar to the levels of complement proteins in the blood, plasma or serum of a rodent that expresses functional endogenous C5 protein. In one embodiment, the rodent is a mouse. In one embodiment, the rodent is a rat.

In one aspect, genetically modified rodents, e.g., a mouse or rat, are provided that express C5 protein from a human C5 gene, wherein the rodent expresses human or humanized C5 protein in its serum. In one embodiment, the rodent is a mouse. In one embodiment, the rodent is a rat.

In one embodiment, the serum of the rodent that expresses a human or humanized C5 protein has approximately the same level of C5 protein as a rodent that expresses a functional, endogenous C5 protein, e.g., a wild-type mouse or rat. In one embodiment, the rodent is a mouse. In one embodiment, the rodent is a rat.

In one embodiment, the mouse expresses human or humanized C5 protein in serum at a concentration of at least about 10%, 20%, 30%, 40%, 50%, 60%, 70%, 80%, 90%, 100%, 110%, 120%, 130%, 140%, 150%, 160%, 170%, 180%, 190% or 200% of the level of C5 protein present in the serum of an age-matched mouse that expresses functional endogenous C5 protein, but does not comprise a replacement of an endogenous C5 gene, at an endogenous mouse C5 locus, with a human C5 gene.

In one embodiment, the mouse expresses human or humanized C5 protein in serum at a concentration of between about 10% and about 200%, between about 20% and about 150%, or between about 30% and about 100% of the level of mouse C5 protein present in the serum of an age-matched mouse that expresses functional endogenous C5 protein, but does not comprise a replacement of an endogenous C5 gene, at an endogenous mouse C5 locus, with a human C5 gene.

In one embodiment, the mouse expresses human or humanized C5 protein in serum at a concentration of between about 10 µg/ml and about 150 µg/ml, between about 10 µg/ml and about 125 or between about 15 µg/ml and about 100 µg/ml.

In one embodiment, the mouse expresses human or humanized C5 protein in serum at a concentration of at least about 10, 20, 30, 40, 50, 60, 70, 80, 90, 100, 125 or 150 µg/ml.

In one aspect, genetically modified rodents, e.g., a mouse or rat, are provided that express a human or humanized C3 protein, wherein the rodent that expresses a human or humanized C3 protein comprises a normal complement system, i.e., the levels of complement proteins in the blood, plasma or serum of the rodent expressing human or humanized C3 protein are similar to the levels of complement proteins in the blood, plasma or serum of a rodent that expresses functional endogenous C3 protein. In one embodiment, the rodent is a mouse. In one embodiment, the rodent is a rat.

In one aspect, genetically modified rodents, e.g., a mouse or rat, are provided that express C3 protein from a human C3 gene, wherein the rodent expresses human or humanized C3 protein in its serum. In one embodiment, the rodent is a mouse. In one embodiment, the rodent is a rat.

In one embodiment, the serum of the rodent that expresses a human or humanized C3 protein has approximately the same level of C3 protein as a rodent that expresses a functional, endogenous C3 protein, e.g., a wild-type mouse or rat. In one embodiment, the rodent is a mouse. In one embodiment, the rodent is a rat.

In one embodiment, the mouse expresses human or humanized C3 protein (hC3) in serum at a concentration of at least about 10%, 20%, 30%, 40%, 50%, 60%, 70%, 80%, 90%, 100%, 110%, 120%, 130%, 140%, 150%, 160%, 170%, 180%, 190% or 200% of the level of C3 protein present in the serum of an age-matched mouse that expresses functional endogenous C3 protein, but does not comprise a replacement of an endogenous C3 gene, at an endogenous mouse C3 locus, with a human C3 gene.

In one embodiment, the mouse expresses human C3 protein in serum at a concentration of between about 10% and about 200%, between about 20% and about 150%, or between about 30% and about 100% of the level of mouse C3 protein present in the serum of an age-matched mouse that expresses functional endogenous C3 protein, but does not comprise a replacement of an endogenous C3 gene, at an endogenous mouse C3 locus, with a human C3 gene.

In one embodiment, the mouse expresses human or humanized C3 protein in serum at a concentration of between about 100 µg/ml and about 1500 µg/ml, between about 200 µg/ml and about 1250 µg/ml, or between about 300 µg/ml and about 1000 µg/ml.

In one embodiment, the mouse expresses human or humanized C3 protein in serum at a concentration of at least about 100, 200, 300, 400, 500, 600, 700, 800, 900, 1000, 1250 or 1500 µg/ml.

In one aspect, a genetically modified rodent is provided, comprising a human C5 gene comprising a replacement at an endogenous rodent C5 locus of a rodent gene encoding C5 protein with a human C5 gene encoding human or humanized C5 protein, wherein expression of the human C5 gene encoding human or humanized C5 protein is under control of rodent regulatory elements or sequences at the endogenous rodent C5 locus, and wherein the rodent further comprises a human C3 gene comprising a replacement at an endogenous rodent C3 locus of a rodent gene encoding C3 protein with a human C3 gene encoding human or humanized C3 protein, wherein expression of the human C3 gene encoding human or humanized C3 protein is under control of rodent regulatory elements or sequences at the endogenous rodent C3 locus. In one embodiment, the rodent is a mouse. In one embodiment, the rodent is a rat.

In one embodiment, the mouse is incapable of expressing a mouse C5 protein and incapable of expressing a mouse C3 protein.

In one embodiment, the rodent regulatory elements or sequences at the endogenous rodent C5 locus and/or rodent C3 locus are from a mouse or a rat.

In one embodiment, the rodent regulatory elements or sequences are endogenous rodent regulatory elements or sequences at the rodent C5 locus and/or rodent C3 locus are from a mouse or a rat.

In one aspect, a non-human animal, e.g., a rodent, e.g., a mouse or rat, is provided that expresses human or humanized C5 and/or C3 proteins, wherein the non-human animal expresses human or humanized C5 and/or C3 proteins from an endogenous non-human C5 locus and/or an endogenous non-human C3 locus. In an embodiment, the non-human animal is a rodent. In an embodiment, the rodent is a mouse. In an embodiment, the rodent is a rat.

In one aspect, a genetically modified mouse is provided that expresses human or humanized C5 protein from an endogenous mouse C5 locus, wherein the endogenous mouse C5 gene has been replaced, in whole or in part, with a human C5 gene.

In one embodiment, about 75.8 kb at the endogenous mouse C5 locus, including exons 2 through 42 and a 3 untranslated sequence, is deleted and replaced with about 97 kb of human C5 gene sequence comprising exons 2 through 41 of the human C5 gene. In a specific embodiment, the human C5 gene comprises exons 2 through 42 of the human C5 gene of human BAC CTD-2559119. In a specific embodiment, the C5 gene comprises mouse C5 exon 1 and human C5 exons 2 through 42.

In one aspect, a genetically modified mouse is provided that comprises a nucleotide sequence encoding a human or humanized C5 protein, wherein the nucleotide sequence encoding the human or humanized C5 protein replaces, in whole or in part, an endogenous nucleotide sequence encoding an endogenous mouse C5 protein.

In one aspect, a genetically modified mouse is provided that expresses human or humanized C3 protein from an endogenous mouse C3 locus, wherein the endogenous mouse C3 gene has been replaced, in whole or in part, with a human C3 gene.

In one embodiment, a portion of the endogenous mouse C3 locus, including 5' regulatory elements upstream of exon 1 through exon 41, is deleted and replaced with a human C3 gene sequence comprising 5' regulatory elements upstream of exon 1 through exon 41 of the human C3 gene. In a specific embodiment, the human C3 gene comprises the entire human C3 coding region.

In one embodiment, a portion of the endogenous mouse C3 locus, including a portion of intron 1 and exons 2 through 41, is deleted and replaced with a human C3 gene sequence comprising a portion of intron 1 and exons 2 through exon 41 of the human C3 gene. In a specific embodiment, the C3 gene comprises mouse C3 exon 1 and human C3 exons 2 through 41.

In one aspect, a method is provided for making a humanized C5 rodent, comprising replacing a rodent C5 gene sequence encoding rodent C5 protein with a human C5 gene sequence comprising one or more exons of the human C5 gene sequence encoding human or humanized C5 protein. In one embodiment, the rodent is a mouse. In one embodiment, the rodent is a rat.

In one embodiment, the replacement is at an endogenous rodent C5 locus and the human C5 gene sequence comprising one or more exons of the human C5 gene sequence encoding human or humanized C5 protein is operably linked to rodent regulatory elements or sequences at the endogenous rodent C5 locus. In one embodiment, the rodent is a mouse. In one embodiment, the rodent is a rat.

In one embodiment, the rodent regulatory elements or sequences are derived from a mouse. In one embodiment, the rodent regulatory elements or sequences are derived from a rat.

In one embodiment, the rodent regulatory elements or sequences are endogenous rodent regulatory elements or sequences at the rodent C5 locus. In one embodiment, the rodent is a mouse. In one embodiment, the rodent is a rat.

In one embodiment, the human C5 gene sequence replacing the rodent C5 gene sequence comprises at least one exon of the human C5 gene sequence. In other embodiments, the human C5 gene sequence replacing the rodent C5 gene sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 exons of the human C5 gene sequence. In one embodiment, the human C5 gene sequence replacing the rodent C5 gene sequence comprises all 41 exons of the human C5 gene sequence. In one embodiment, the rodent is a mouse. In one embodiment, the rodent is a rat.

In one embodiment, the replacement is at an endogenous rodent C5 locus and the human C5 gene sequence comprising one or more exons of the human C5 gene sequence encoding human or humanized C5 protein is operably linked endogenous rodent regulatory elements or sequences at the endogenous rodent C5 locus.

In one aspect, a method is provided for making a humanized C5 mouse, comprising replacing a mouse C5 gene sequence encoding mouse C5 protein with a human C5 gene sequence encoding human or humanized C5 protein.

In one embodiment, the replacement is at an endogenous mouse C5 locus, and the human C5 gene encoding human or humanized C5 protein is operably linked to mouse regulatory elements or sequences at the endogenous mouse C5 locus.

In one embodiment, the replacement is at an endogenous mouse C5 locus, and the human C5 gene encoding human or humanized C5 protein is operably linked to endogenous mouse regulatory elements or sequences at the endogenous mouse C5 locus.

In one aspect, a method is provided for making a humanized C3 rodent, comprising replacing a rodent C3 gene sequence encoding rodent C3 protein with a human C3 gene sequence comprising one or more exons of the human C3 gene sequence encoding human or humanized C3 protein. In one embodiment, the rodent is a mouse. In one embodiment, the rodent is a rat.

In one embodiment, the replacement is at an endogenous rodent C3 locus and the human C3 gene sequence comprising one or more exons of the human C3 gene sequence encoding human or humanized C3 protein is operably linked to rodent regulatory elements or sequences at the endogenous rodent C3 locus. In one embodiment, the rodent is a mouse. In one embodiment, the rodent is a rat.

In one embodiment, the rodent regulatory elements or sequences are derived from a mouse. In one embodiment, the rodent regulatory elements or sequences are derived from a rat.

In one embodiment, the rodent regulatory elements or sequences are endogenous rodent regulatory elements or sequences at the rodent C3 locus. In one embodiment, the rodent is a mouse. In one embodiment, the rodent is a rat.

In one embodiment, the human C3 gene sequence replacing the rodent C3 gene sequence comprises at least one exon of the human C3 gene sequence. In other embodiments, the human C3 gene sequence replacing the rodent C3 gene sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 exons of the human C3 gene sequence. In one embodiment, the human C3 gene sequence replacing the rodent C5 gene sequence comprises all 41 exons of the human C3 gene sequence. In one embodiment, the rodent is a mouse. In one embodiment, the rodent is a rat.

In one embodiment, the replacement is at an endogenous rodent C3 locus and the human C3 gene sequence comprising one or more exons of the human C3 gene sequence encoding human or humanized C3 protein is operably linked endogenous rodent regulatory elements or sequences at the endogenous rodent C3 locus.

In one aspect, a method is provided for making a humanized C3 mouse, comprising replacing a mouse C3 gene sequence encoding mouse C3 protein with a human C3 gene sequence encoding human or humanized C3 protein.

In one embodiment, the replacement is at an endogenous mouse C3 locus, and the human C3 gene encoding human or humanized C3 protein is operably linked to endogenous mouse regulatory elements or sequences at the endogenous mouse C3 locus.

In one embodiment, the replacement is at an endogenous mouse C3 locus, and the human C3 gene encoding human or humanized C3 protein is operably linked to mouse regulatory elements or sequences at the endogenous mouse C3 locus.

In various aspects, the genetically modified non-human animals, e.g., rodents, e.g., mice or rats, described herein comprise the genetic modifications in their germ-line.

In one aspect, a non-human animal, e.g., rodent, e.g., a mouse or rat, embryo comprising a genetic modification as described herein is provided.

In one aspect, a non-human animal, e.g., rodent, e.g., a mouse or rat, host embryo is provided that comprises a donor cell that comprises a genetic modification as described herein.

In one aspect, a pluripotent or totipotent non-human animal, e.g., rodent, e.g., mouse or rat, cell comprising a genetic modification as described herein is provided. In one embodiment, the cell is a rodent cell. In one embodiment, the cell is a mouse cell. In one embodiment, the cell is a rodent ES cell. In one embodiment, the cell is a mouse ES cell.

In one aspect, a non-human animal, e.g., rodent, e.g., mouse or rat, egg is provided, wherein the non-human animal egg comprises an ectopic non-human animal chromosome, wherein the ectopic non-human animal chromosome comprises a genetic modification as described herein. In one embodiment, the non-human animal is a rodent. In one embodiment, the rodent is a mouse. In one embodiment, the rodent is a rat.

In one aspect, the mouse embryo, egg, or cell that is genetically modified to comprise a human C5 gene or human C3 gene is of a mouse that is of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/O1a. In another embodiment, the mouse is a 129 strain selected from the group consisting of a strain that is 129P1, 129P2, 129P3, 129X1, 129S1 (e.g., 12951/SV, 129S1/Svlm), 129S2, 129S4, 129S5, 129S9/SvEvH, 12956 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. In one embodiment, the mouse is Swiss or Swiss Webster mouse.

In a further aspect, provided herein are methods for identifying a compound capable of modulating complement activation comprising administering the compound to any of the non-human animals, e.g., a rodent, e.g., a mouse or rat disclosed and described herein; and assaying if complement activation in the rodent is modulated, thereby identifying a compound capable of modulating complement activation. In one embodiment, the compound is a small molecule chemical compound, an antibody, a protein, an inhibitory nucleic acid, or any combination thereof. In another embodiment of any of the embodiments disclosed herein, the compound modulates complement activation by increasing complement activity. In another embodiment of any of the embodiments disclosed herein, the compound modulates complement activation by decreasing complement activity. In another embodiment of any of the embodiments disclosed herein, the serum of the rodent is assayed to determine if complement activation in the rodent is modulated. In a further embodiment, the assay is a $CH_{50}$ complement screening assay.

Each of the aspects and embodiments described herein are capable of being used together, unless excluded either explicitly or clearly from the context of the embodiment or aspect.

DETAILED DESCRIPTION

Figure 1:
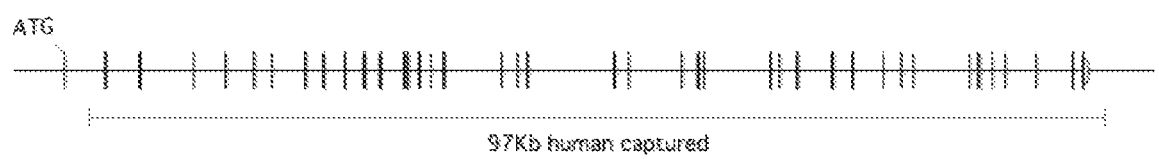
FIG. 1 provides an illustration, not to scale, of the mouse (top) and human (bottom) C5 genomic loci. The regions of the mouse and human C5 genes that are deleted and replaced, respectively, to generate humanized C5 mice are indicated.
Figure 1:
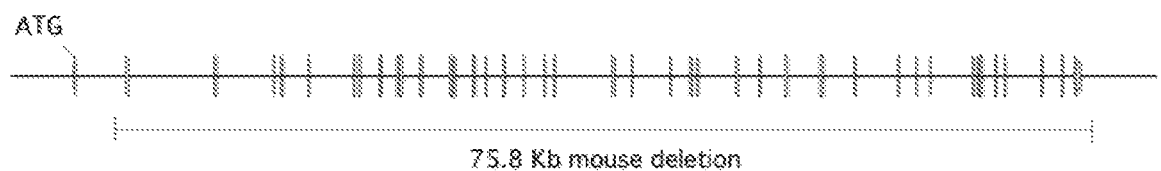

The complement system is an essential component of the innate immune system and plays a critical role as a defense mechanism against invading pathogens, primes adaptive immune responses, and helps remove immune complexes and apoptotic cells. While the complement system plays a critical role in many protective immune functions, complement activation is a significant mediator of tissue damage in a wide range of autoimmune and inflammatory disease processes.

The invention described herein provides, inter alia, non-human animals that express human or humanized C5 and/or C3 proteins in serum at concentrations similar to wild type expression of endogenous C5 and/or C3 proteins in non-human animals. The successful engineering of non-human animals capable of expressing human or humanized C5 and/or C3 proteins provides a needed and useful tool for recapitulating the human complement system in laboratory animals amenable to large scale and high-throughput drug screening assays. Also provided herein are methods for using the non-human animals (such as rodents) described herein for identifying compounds capable of modulating complement activation. The methods are based, in part, on the inventors' discovery that while complement activity of C5 protein is species-specific (i.e., human C5 protein is unable to substitute for mouse C5 protein), the complement activity of human C3 protein is able to substitute for mouse C3 protein in a mouse serum complement activity.

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, N.Y. (Greenfield, ed., 2014), Beaucage et al. eds., *Current Protocols in Nucleic Acid Chemistry*, John Wiley & Sons, Inc., New York, 2000, (including supplements through 2014) and *Gene Transfer and Expression in Mammalian Cells* (Makrides, ed., Elsevier Sciences B.V., Amsterdam, 2003).

Definitions

As used herein, the term "protein" includes polypeptides, peptides, fragments of polypeptides, and fusion polypeptides.

As used herein, a "nucleic acid" refers to two or more deoxyribonucleotides and/or ribonucleotides covalently joined together in either single or double-stranded form.

By "operably linked" is meant a functional linkage between a nucleic acid expression control sequence (such as a promoter) and a second nucleic acid sequence, wherein the expression control sequence directs transcription of the nucleic acid corresponding to the second sequence.

The term "replacement" in reference to gene replacement refers to placing exogenous genetic material at an endogenous genetic locus, thereby replacing all or a portion of the endogenous gene with an orthologous or homologous nucleic acid sequence. In one instance, an endogenous non-human gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous non-human gene or fragment thereof that is replaced. As demonstrated in the Examples below, nucleotide sequences of endogenous non-human (for example rodent, such as, mouse) C3 and/or C5 gene loci were replaced by nucleotide sequences corresponding to human C3 and/or C5 gene loci. In another embodiment, a gene replacement can occur when an endogenous gene is deleted or rendered nonfunctional (such as by the insertion of a missense mutation or a premature stop codon) and a corresponding human gene or fragment thereof is inserted into the germ line at a separate location.

The term "humanized" as used in the phrases "humanized C3 allele" or "humanized C5 allele," or "humanized C3 gene," or "humanized C5 gene" includes, but is not limited to, embodiments wherein all or a portion of an endogenous non-human C3 and/or C5 gene or allele is replaced by a corresponding portion of the human C3 and/or C5 gene or allele. For example, in some embodiments, the term "humanized" refers to the complete replacement of the coding region (e.g., the exons) of the endogenous non-human C3 and/or C5 gene or allele with the corresponding coding region of the human C3 and/or C5 gene or allele, while the endogenous non-coding region(s) (such as, but not limited to, the promoter, the 5' and/or 3' untranslated region(s), enhancer elements, etc.) of the non-human animal is not replaced. In some embodiments, the non-human animal is a rodent, such as a rat or mouse.

A "humanized protein" includes, but is not limited to, embodiments wherein all or a portion of the encoded endogenous non-human C3 and/or C5 protein is replaced by the corresponding portion of the human C3 and/or C5 protein. In some embodiments, a "humanized protein" can be encoded by a humanized C3 and/or C5 gene or allele but still encode a fully human C3 and/or C5 protein (such as, but not limited to, the situation wherein all of the coding regions (e.g., the exons) of the endogenous non-human C3 and/or C5 gene or allele are replaced by the corresponding coding regions of the human C3 and/or C5 gene or allele but the endogenous non-coding region(s) (such as, but not limited to, the promoter, the 5' and/or 3' untranslated region(s), enhancer elements, etc.) of the non-human animal is not replaced). In some embodiments, the non-human animal is a rodent, such as a rat or mouse.

"Modulates," as used herein, refers to the ability of a compound to alter the activity of the complement system. In one embodiment, modulation of the complement system by a compound refers to decreasing complement activation in a subject (for example, a rodent, such as a mouse). In another embodiment, modulation of the complement system by a compound refers to increasing complement-mediated activity in a subject.

As used herein, the term "rodent" refers to any member of the order Rodentia. Examples of rodents include, without limitation, mice, rats, squirrels, prairie dogs, porcupines, beavers, guinea pigs, and hamsters. In one embodiment, a rodent is a rat. In another embodiment, a rodent is a mouse.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Complement System

Complement, an essential component of the immune system, consists of more than 30 serum and cellular proteins that are involved in two linked biochemical cascades, the classical and alternative pathways. Complement functions to assist the immune system to destroy invading microorganisms and maintain tissue homeostasis.

However, excessive or unregulated activation of complement contributes to tissue damage, and is associated with a variety of variety of human diseases, disorders and conditions that are associated with complement activation, for example, ocular inflammatory and retinal degenerative diseases (see Makrides (1998) Therapeutic inhibition of the complement system, *Pharmacological Reviews* 50(1):59-87; and Mollnes et al. (2006) Strategies of therapeutic complement inhibition, *Molecular Immunology* 43; 107-121). Other diseases or conditions known to be associated with aberrant complement activation include, without limitation, allergic asthma and the accompanying airway inflammation and airway hyperresponsiveness ("AHR"), chronic obstructive pulmonary disease ("COPD"), allergic bronchopulmonary aspergillosis, hypersensitivity pneumonia, eosinophilic pneumonia, emphysema, bronchitis, allergic bronchitis, bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection and adenovirus infection, and ischemic-reperfusion injury (see, e.g., U.S. Patent Application Publication No. 2005/0260198, which is incorporated herein by reference).

Complement C5 Gene and Protein

The C5 gene encodes the serum complement C5 protein, which plays an important role in inflammatory and cell killing processes. Mature C5 protein is comprised of $\alpha$ and $\beta$ chains that are linked by a disulfide bond. The C5 protein is cleaved by a convertase, resulting in an activation peptide, C5a, an anaphylatoxin derived from the $\alpha$ polypeptide, which is largely pro-inflammatory, and C5b, a macromolecular cleavage product derived from the $\beta$ polypeptide, which forms a complex with other complement components to form a membrane attack complex (MAC), which is involved in osmotic lysis of target cells.

Human C5. Official symbol: C5; NCBI Gene ID: 727; Primary source: HGNC:1331; RefSeq mRNA ID:

NM_001735.2; UniProt ID: P01031; Genomic assembly: GRCh38; Location: chr9:120,952,335-121,050,275—strand.

The human C5 gene is located on chromosome 9, at 9q33-q34. The human C5 gene has 41 exons and encodes a precursor polypeptide of 1676 amino acids in length, including an 18 amino acid signal peptide, a 655 amino acid β chain and a 999 amino acid α chain. During complement activation the α chain is cleaved, thereby generating a 74 amino acid C5a, which is a potent pro-inflammatory anaphylatoxin.

C5 deficiency in humans is associated with increased susceptibility to severe recurrent infections.

The C5 gene is conserved between several species, including primates, e.g., chimpanzee, Rhesus monkey, other mammals, e.g., dog, cow, rodent, e.g., mouse, chicken, zebrafish and frog.

Mouse C5. Official symbol: Hc; NCBI Gene ID: 15139; Primary source: MGI:96031; RefSeq mRNA ID: NM_010406.2; UniProt ID: P06684; Genomic assembly: GRCm38; Location: chr2:34,983,331-35,061,449—strand.

The mouse C5 gene is located on chromosome 2, at 2 23.22 cM. The mouse C5 gene has 42 exons and encodes a precursor polypeptide of 1680 amino acids in length, including an 18 amino acid signal peptide, a 656 amino acid β chain and a 1002 amino acid α chain. During complement activation the α chain is cleaved, thereby generating a 77 amino acid C5a, which is a potent pro-inflammatory anaphylatoxin.

C5 deficiency is observed in several common strains of laboratory mice which have a common 2 base pair deletion near the 5' end of the cDNA that results in inability of C5 to be secreted; thus, these mice are functionally C5 deficient, i.e., C5 knockouts (6 such strains are A/HeJ, AKR/J, DBA/2J, NZB/B1NJ, SWR/J, and B10.D2/oSnJ) (see, e.g., Wetzel et al. (1990) Deficiency of the murine fifth complement component (C5): a 2-base pair deletion in a 5' exon, *J Biol Chem* 265:2435-2440). C5 knockout mice can also be generated following standard procedures known in the art.

Complement C3 Gene and Protein

The C3 gene encodes the serum complement protein C3, which plays a central role in the activation of the classical and alternative complement activation pathways.

The human C3 gene is located on chromosome 19 at 19p13.3-p13.2. The human C3 gene has 41 exons and encodes a precursor polypeptide of 1663 amino acids, including a 22 amino acid signal peptide, a 645 amino acid β chain and a 992 amino acid α chain. During complement activation the α chain is cleaved, thereby generating 9 different peptides, including a 77 amino acid C5a, which is a potent pro-inflammatory anaphylatoxin.

C3 deficiency in humans is associated with increased susceptibility to bacterial infections.

The C3 gene is conserved between several species, including primates, e.g., chimpanzee, Rhesus monkey, other mammals, e.g., dog, cow, rodent, e.g., mouse, chicken, zebrafish and frog.

The mouse C3 gene is located on chromosome 17 at 17 29.72 cM19, The mouse C3 gene has 41 exons and encodes a precursor polypeptide of 1663 amino acids, including a 24 amino acid signal peptide, a 642 amino acid β chain and a 993 amino acid α chain. During complement activation the α chain is cleaved, thereby generating 9 different peptides, including a 78 amino acid C3a, which is a potent pro-inflammatory anaphylatoxin.

C3 knockout mice have been generated following standard procedures known in the art (see, e.g., Drouin et al. (2001) Cutting edge: the absence of 3 demonstrates a role for complement in Th2 effector functions in a murine model of pulmonary allergy, *J Immunology* 167:4141-4144).

Species Specificity of C5 and C3 Complement Proteins

Shown herein, humanized C5 mice are functionally C5 deficient because at least some of the endogenous complement proteins display species-specificity, i.e., the endogenous mouse complement proteins are unable to functionally interact with the human C5 protein. Serum obtained from humanized C5 mice or C5 knockout mice were tested for complement activity; no complement hemolytic activity was observed unless both human C3 and human C5 proteins were added.

Also shown herein, addition of human C3 to sera obtained from C3 knockout mice was able to rescue hemolytic function; complement activity was observed in C3 knockout mice when human C3 protein was added to serum.

The complement activity of C5 protein is species-specific, i.e., human C5 protein is unable to substitute for mouse C5 protein in a mouse serum complement activity (i.e., hemolysis) assay.

The complement activity of C3 protein, in contrast does not appear to be similarly species-specific, i.e., human C3 protein is able to substitute for mouse C3 protein in a mouse serum complement activity (i.e., hemolysis) assay.

Therapeutic Inhibition of the Complement System

Two targets for therapeutic complement inhibition are the complement activation peptides C5a and C3a, which are generated upon complement activation by enzymatic cleavage in both the classical and alternative pathways from complement proteins C5 and C3, respectively (see Markides (1998); Molines et al. (2006)).

For example, blocking C5 cleavage by antibodies, for example, antibodies disclosed in U.S. Pat. No. 6,355,245, is a possible therapeutic strategy for complement inhibition in diseases associated with complement activation.

Species Specificity of Human C5 and C3 Inhibitors

Candidate therapeutic molecules that target the complement proteins C5 or C3 are typically evaluated for pharmacokinetics (PK) and pharmacodynamics (PK) in non-human animals, e.g., rodents, e.g., mice or rats. Such therapeutic molecules are also tested for in vivo therapeutic efficacy in non-human animal, e.g., rodent, e.g., mouse or rat, models of human diseases, disorders and conditions associated with complement activation.

However, therapeutic molecules, which are specific for the human complement proteins C5 or C3, i.e., human-specific C5 or C3 inhibitors, cannot be adequately evaluated for PD or in vivo therapeutic efficacy in rodents, in particular mice, because the targets of these therapeutic molecules are missing. This problem is not overcome using transgenic non-human animals, e.g., rodents, e.g., mice or rats, expressing human C5 or C3 complement proteins because of the above-mentioned species specificity of these proteins.

Accordingly, to assess the PD and in vivo therapeutic efficacy of a human-specific C5 or C3 protein antagonist or inhibitor in non-human animals, e.g., rodents, e.g., mice or rats, it is desirable to replace the endogenous C5 and/or C3 proteins with human C5 and/or C3 proteins. Moreover, in order to avoid potential problems of over- or under-expression of the human C5 and/or C3 proteins, it is desirable to insert the human C5 and/or C3 genes into the genome of the non-human animals, e.g., rodents, e.g., mice or rats, at the endogenous C5 and/or C3 gene loci, and to express the human C5 and/or C3 proteins in non-human animals, e.g., rodents, e.g., mice or rats, under the control, at least in part, of the endogenous C5 and/or C3 regulatory elements.

Creation of Humanized C3 and/or C5 Non-Human Animals

Methods for generating the humanized C3 and/or C5 animals of the present invention are well known in the art (see, generally, Gene Targeting: A Practical Approach, Joyner, ed., Oxford University Press, Inc. (2000)). In one embodiment, generation of the mice may optionally involve disruption of murine C3 and/or C5 genes and introduction of the gene encoding human or humanized C3 and/or C5 into the murine genome. In one embodiment, the introduction of the gene encoding human or humanized C3 and/or C5 is at the same location as the endogenous murine C3 and/or C5 genes.

The transgenic non-human animals of the invention can be produced by introducing transgenes into the germ line of the animal. Embryonic target cells at various developmental stages can be used to introduce transgenes. Different methods are used depending on the stage of development of the embryonic target cell. The specific line(s) of any animal used to practice this invention are selected for general good health, good embryo yields, good pronuclear visibility in the embryo, and good reproductive fitness. When transgenic mice are to be produced, strains such as C57BL/6 or C57BL/6×DBA/2 $F_1$, or FVB lines are often used (obtained commercially from Charles River Labs, Boston, Mass., The Jackson Laboratory, Bar Harbor, Me., or Taconic Labs.).

Introduction of the transgene into the embryo can be accomplished by any means known in the art such as, for example, microinjection, electroporation, or lipofection. For example, the transgene(s) can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this invention. One common method is to incubate the embryos in vitro for about 1-7 days, depending on the species, and then reimplant them into the surrogate host.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260-1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927-6931; Van der Putten et al. (1985) *PNAS* 82:6148-6152).

A third type of target cell for transgene introduction is the embryonic stem (ES) cell. Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal.

Transgenic animals comprising humanized C3 and/or C5 can be crossed with other animals. A manner of preparation is to generate a series of mammals, each containing one of the desired constructs or transgenes. Such mammals are bred together through a series of crosses, backcrosses and selections, to ultimately generate a single mammal containing all desired constructs and/or transgenes, where the mammal is otherwise congenic (genetically identical) to the wild type except for the presence of the desired constructs and/or transgene(s). In one embodiment, a mouse comprising a human or humanized C3 and/or C5 gene is produced in this manner.

Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. In addition, it may be necessary to cross or backcross over several generations to ultimately obtain the desired genotype.

Use of Humanized C3 and/or C5 Non-human Animals for Identifying Compounds Capable of Modulating the Complement System In some aspects, provided herein are methods for identifying a candidate therapeutic molecule (i.e. a compound) capable of modulating complement activation. The method utilizes any of the humanized C3 and/or C5 rodents (for example, mice or rats) disclosed herein. In some embodiments, candidate compounds are administered directly to the rodents following experimental induction of complement activation (for example, in a kidney ischemia/reperfusion model) and the effects of said compounds with respect to their ability to modulate the complement system are assessed. In other embodiments, candidate compounds are contacted with serum obtained from these animals and complement activity is assessed using any commonly used in vitro assessment technique (such as, but not limited to $CH_{50}$ assays).

In some embodiments, the candidate compound can modulate complement activation by reducing, decreasing, or inhibiting complement activation. The compound may reduce complement activation in any of the rodents disclosed herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rodents that are not treated with the candidate compound.

In another embodiment, the candidate compound can reduce, decrease, or inhibit complement activation for up to 1 hour, 2 hours, 3 hours, 4 hours, 5 hours, 6 hours, 7 hours, 8 hours, 9 hours, 10, hours, 11, hours, 12 hours, 18 hours, 24 hours, 30 hours, 36 hours, 42 hours, 48 hours, 54 hours, 60 hours, 66 hours, 72 hours, 4 days, 5 days, 6 days, 7 days, 8 days, 9 days, 10 days, 11 days, 12 days, 13 days, 14 days, or three weeks, inclusive (including any periods of time in between these values).

The candidate compound can further modulate complement activation in other embodiments by increasing, amplifying or activating complement activity. The compound may increase complement activation in any of the rodents disclosed herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51% 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rodents that are not treated with the candidate compound.

In another embodiment, the candidate compound can increase, amplify or activate complement activity for up to 1 hour, 2 hours, 3 hours, 4 hours, 5 hours, 6 hours, 7 hours, 8 hours, 9 hours, 10, hours, 11, hours, 12 hours, 18 hours, 24 hours, 30 hours, 36 hours, 42 hours, 48 hours, 54 hours, 60 hours, 66 hours, 72 hours, 4 days, 5 days, 6 days, 7 days, 8 days, 9 days, 10 days, 11 days, 12 days, 13 days, 14 days, or three weeks, inclusive (including any periods of time in between these values).

Candidate compounds can be, without limitation, small molecule chemical compounds, antibodies, proteins, inhibitory nucleic acids, or any combination thereof.

1. Antibodies

In some aspects, the candidate compound binds (such as preferentially binds) to a complement protein (such as, but not limited to, C5 or C3 (e.g. C3a)) and is an antibody. In some embodiments, the antibodies are C5 and/or C3 antagonists and can decrease complement activation. In other embodiments, the antibodies are C5 and/or C3 agonists and can increase complement activation.

Variants of antibodies can also be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Nucleic acid molecules encoding amino acid sequence variants of the antibody can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

Fc region variants with altered (i.e. improved or diminished) C1q binding and/or Complement Dependent Cytotoxicity (CDC) are described in International Patent Application Publication No.: WO99/51642 (incorporated herein by reference). Such variants may comprise an amino acid substitution at one or more of amino acid positions of the Fc region. See, also, Duncan & Winter, *Nature* 322:738-40 (1988); U.S. Pat. Nos. 5,648,260; 5,624,821; and International Patent Application Publication No. WO94/29351 concerning Fc region variants, the disclosures of each of which are incorporated by reference herein.

2. Non-Antibody Binding Polypeptides

In some aspects, the candidate compound binds (such as preferentially binds) to a complement protein (such as, C5 or C3 (e.g. C3a)) and is a non-antibody binding polypeptide. In some embodiments, the non-antibody binding polypeptide is a C5 and/or C3 antagonist and can decrease complement activation. In other embodiments, the non-antibody binding polypeptide is a C5 and/or C3 agonist and can increase complement activation.

Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding to a target, such as any of the complement proteins (e.g. C5 or C3) discussed herein.

Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Application Publication Nos. WO 84/03506 and WO84/03564; Geysen et al, *Proc. Natl. Acad, Sci, U.S.A.*, 81:3998-4002 (1984); Geysen et al, *Proc. Nati. Acad. Sci. U.S.A.*, 82: 178-182 (1985); Geysen et al., *J. Immunol. Meth.*, 102:259-274 (1987); Clackson, T. et al., (1991) Nature, 352: 624; Kang, A. S. et al., (1991) Proc. Natl. Acad. Sci. USA, 88:8363, and Smith, G. P. (1991) Current Opin. Biotechnol, 2:668, the disclosures of each of which are incorporated by reference herein.

Methods for generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323, the disclosures of each of which are incorporated by reference herein.

Binding polypeptides can be modified to enhance their inhibitory and/or therapeutic effect (including, for example, enhanced affinity, improved pharmacokinetic properties such as half-life, stability, and clearance rate, reduced toxicity, etc.). Such modifications include, without limitation, glycosylation, pegylation, substitution with non-naturally occurring but functionally equivalent amino acid, linking groups, etc.

3. Small Molecules

In some aspects, the candidate compound binds (such as preferentially binds) to a complement protein (such as, C5 or C3 (e.g. C3a)) and is a small molecule. In some embodiments, the small molecule is a C5 and/or C3 antagonist and can decrease complement activation. In other embodiments, the small molecule is a C5 and/or C3 agonist and can increase complement activation.

Small molecules are preferably organic molecules other than binding polypeptides or antibodies as defined herein. Organic small molecules may be identified and chemically synthesized using known methodology (see, e.g., PCT Application Publication Nos. WO 00/00823 and WO 00/39585). Organic small molecules are usually less than about 2000 Daltons in size, alternatively less than about 1500, 750, 500, 250 or 200 Daltons in size, wherein such organic small molecules that are capable of binding to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Application Publication Nos. WO 00/00823 and WO 00/39585).

Organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding a target molecule (for example, C5 and/or C3) or mediating a biological activity of interest (such as, but not limited to, inhibition or activation of complement activity).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports.

To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

The small molecule agents described in any of the aspects herein can be derived from any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclo-condensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports, can be found in U.S. Patent Application No. 2009/0032592; Needels et al., (1993), *Proc. Natl. Acad. Sci. USA* 90: 10700-10704; and PCT Application Publication No. WO 97/15390, the disclosures of which are incorporated by reference herein.

4. Inhibitory Nucleic Acids

In one aspect of this invention, the candidate complement modulatory compound is one or more oligonucleotides targeted to a component (such as an mRNA) of the complement system. The inhibitory nucleic acid can be, without limitation, any of an antisense oligonucleotide, a small inhibitory RNA (siRNA), or a ribozyme.

The oligonucleotide of the invention may be an mRNA encoding a protein component of the complement system. The oligonucleotides will bind to the mRNAs and interfere with their functions, either by mediating their destruction or by preventing translation into proteins. Absolute complementarity, although preferred, is not required. An oligonucleotide sequence "complementary" to a portion of an RNA, as referred to herein, means a sequence having sufficient complementarity to be able to hybridize with the RNA, forming a stable duplex. The ability to hybridize will depend on both the degree of complementarity and the length of the oligonucleotide. Generally, the longer the hybridizing nucleic acid, the more base mismatches with an RNA it may contain and still form a stable duplex. Those skilled in the art can ascertain a tolerable degree of mismatch by use of standard procedures to determine the melting point of the hybridized complex.

In general, complementary oligonucleotides manufactured to hybridize with mRNAs for proteins of the complement system are targeted to any region of the mRNA, including to the 5' untranslated region of the mRNA, to the complement of the AUG start codon, or to the 3' untranslated region.

The oligonucleotides can have alternate internucleoside linkages, such as, but not limited to, phosphorothioate (Mag at al., *Nucleic Acids Res.* 19:1437-1441, 1991; and U.S. Pat. No. 5,644,048), peptide nucleic acid or PNA (Egholm, *Nature,* 3685:566-568, 1993; and U.S. Pat. No. 6,656,687), phosphoramide (Beaucage, *Methods Mol. Biol.* 20:33-61, 1993), phosphorodithioate (Capaldi et al., *Nucleic Acids Res.,* 28:E40, 2000). Other oligonucleotide analogs include such as, but not limited to, morpholino (Summerton, *Biochim. Biophys. Acta,* 1489:141-158, 1999), locked oligonucleotides (Wahlestedt et al., *Proc. Natl. Acad. Sci. USA,* 97:5633-5638, 2000), peptidic nucleic adds or PNA (Nielsen et al., 1993; Hyrup and Nielsen, 1996) or 2-o-(2-methoxy) ethyl modified 5' and 3' end oligonucleotides (McKay et al., J. Biol. Chem., 274:1715-1722, 1999). All of these references are hereby expressly incorporated by reference. The nucleic acids may contain any combination of deoxyribo- and ribo-nucleotides, and any combination of bases, including uracil, adenine, thymine, cytosine, guanine, inosine, xathanine hypoxathanine, isocytosine, isoguanine, etc.

The complementary oligonucleotides according to the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine. N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)$_w$, and 2,6-diaminopurine The complementary oligonucleotides may also comprise at least one modified sugar moiety selected from the group including but not limited to arabinose, 2-fluoroarabinose, xylulose, and hexose.

The complementary oligonucleotides should be at least ten nucleotides in length, and may range from 10 to about 50 nucleotides in length, such as 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

Assessing Efficacy of Candidate Compounds

Therapeutic efficacy of candidate complement modulatory compounds, appropriate dosages, and methods of the present invention in a given non-human animal (such as a rodent, e.g., a mouse or a rat), can be determined in accordance with in vitro complement assays well known to those having ordinary skill in the art. The complement pathway generates numerous specific products during the normal course of activation and sensitive and specific assays have been developed and are available commercially for most of these activation products, including the small activation fragments C3a, C4a, and C5a and the large activation fragments Bb and sC5b-9. Most of these assays utilize monoclonal antibodies that react with new antigens exposed on the complement fragment, but not on the native proteins from which they are formed, making these assays very simple and specific. ELISA technology is particularly common, although radioimmunoassay (RIA) is also used for detection of C3a and C5a. These latter assays measure both the unprocessed fragments and their processed fragments (i.e., the major forms found in the circulation). Measurement of C3a provides a sensitive, pathway-independent indicator of complement activation. Detection of the fluid-phase product of membrane attack pathway activation, sC5b-9, provides evidence that complement is being activated to completion. Further, the classical pathway also generates C4a, measurement of which provides information about the activity of C3b inhibitor and whether such an inhibitor is activating the classical pathway.

In addition, several in vivo models of complement activation are also available to the skilled artisan for assessing a candidate compound's ability to modulate the complement system. For example, the complement system is implicated in ischemia-reperfusion injury which is sustained after an ischemic event and subsequent restoration of blood flow. Examples of injuries that can cause ischemia-reperfusion injury include, without limitation, myocardial infarction, cerebral ischemic events, intestinal ischemia, and many aspects of vascular surgery, cardiac surgery, trauma, and transplantation. Activation of the complement system plays a role in the inflammatory events of ischemia-reperfusion injury. The ischemia injury results in alterations of the cell membrane, affecting lipids, carbohydrates, or proteins of the external surface such that these exposed epitopes are altered and can act as neo-antigens (modified self antigens). The involvement of the classical pathway of complement to ischemia-reperfusion injury is evidenced by mice genetically deficient in either C3 or C4 that display equal protection from local injury in a hindlimb and animal model of injury (Austen et al. (2003) *Int J Immunopath* Pharm 16:1). Additionally, complement activation has also been shown be involved in a kidney model of ischemia injury (Guo et al. (2005) *Ann Rev Immunol* 23:821).

The invention can be further understood by reference to the following examples, which are provided by way of illustration and are not meant to be limiting.

EXAMPLES

Example 1

Replacement of the Endogenous Mouse C5 Gene with a Human C5 Gene

The 97 kb human C5 gene containing coding exons 2 through 42 of the human C5 gene replaced 75.8 kb of the murine C5 gene locus spanning coding exons 2 through 41 and including a portion of the 3' untranslated region. See FIG. 1.

A targeting construct for replacing the mouse with the human C5 gene in a single targeting step was constructed using VelociGene® genetic engineering technology (see Valenzuela et al. (2003) High-throughput engineering of the mouse genome coupled with high-resolution expression analysis, Nature Biotech, 21(6):652-659). Mouse and human C5 DNA were obtained from bacterial artificial chromosome (BAC) clones bMQ-2277L16 and CTD-2559119, respectively. Briefly, a linearized targeting construct generated by gap repair cloning containing mouse C5 upstream and downstream homology arms flanking a 97 kb human C5 sequence extending from intron 1 just upstream of coding exon 2 through coding exon 41 and the 3' untranslated region (genomic coordinates: GRCh38: chr9:120,952,335-121,050,276 (-strand)) and a fluxed neo selection cassette, was electroporated into F1H4 mouse embryonic stem (ES) cells (C57BL/6×129 F1 hybrid). Correctly targeted ES cells (MAID 7140) were further electroporated with a transient Cre-expressing vector to remove the drug selection cassette. Targeted ES cell clones without drug cassette (MAID 7141) were introduced into an 8-cell stage SW mouse embryo by the VelociMouse® method (see, U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses Nature Biotech, 25(1):91-99). VelociMice® (F0 mice fully derived from the donor ES cell) bearing the humanized C5 gene were identified by genotyping for loss of mouse allele and gain of human allele using a modification of allele assay (see, Valenzuela et al. (2003)).

Correctly targeted ES cell clones were identified by a loss-of-native-allele (LONA) assay (Valenzuela et al. 2003) in which the number of copies of the native, unmodified C5 gene were determined by two TaqMan™ quantitative polymerase chain reactions (qPCRs) specific for sequences in the mouse C5 gene that were targeted for deletion. The qPCR assays comprised the following primer-probe sets (written 5' to 3'): upstream forward primer, CCTCCGGTTA ACTG-GTTTGT GAT (SEQ ID NO:1); upstream reverse primer, GCAGTGAATG GTAGACTTCC CA (SEQ ID NO:2); upstream probe, FAM-AGTGACTTTA CTTTGGTTGT TCTGCTCACA-BHQ (SEQ ID NO:3); downstream forward primer, CCGGGAAAGG AAACCAAGAC (SEQ ID NO:4); downstream reverse primer, CAGCACAGAC TGAGGATCCA A (SEQ ID NO:5); downstream probe, FAM-AGACTGTCAT TCTGGCCCGG ACCT-BHQ (SEQ ID NO:6); in which FAM refers to the 5-carboxyfluorescein fluorescent probe and BHQ refers to the fluorescence quencher of the black hole quencher type (Biosearch Technologies). DNA purified from ES cell clones that have taken up the targeting vector and incorporated in their genomes was combined with TaqMan™ Gene Expression Master Mix (Life Technologies) according to the manufacturer's suggestions in a 384-well PCR plate (MicroAmp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream C5-specific qPCRs and two qPCRs for non-targeted reference genes were run for each DNA sample. The differences in the Ct values (ΔCt) between each C5-specific qPCR and each reference gene qPCR were calculated, and then the difference between each ΔCt and the median ΔCt for all samples assayed was calculated to obtain ΔΔCt values for each sample. The copy number of the C5 gene in each sample was calculated from the following formula: copy number=$2 \times 2^{-\Delta\Delta Ct}$. A correctly targeted clone, having lost one of its native copies, will have a C5 gene copy number equal to one. Confirmation that the human C5 gene sequence replaced the deleted mouse C5 gene sequence in the humanized allele was confirmed by a TaqMan™ qPCR assay that comprises the following primer-probe sets (written 5' to 3'): human upstream forward primer, TGCTCT-TAAA GGACCATCAT CAC (SEQ ID NO:7); human upstream reverse primer, GTAAACGGAT AACG-GAAAGG ATAGA (SEQ ID NO:8); human upstream probe, FAM-CCATTTCCAA ATGCACTTCC CAGC-BHQ (SEQ ID NO:9); human downstream forward primer, CCCACT-GAAC TATCACAGGA AACA (SEQ ID NO:10); human downstream reverse primer, GGAGATGCAT TCCA-GTCTCT GTTA (SEQ ID NO:11); human downstream probe, FAM-TGAAGATGAC CTCCGGATGT AACGG-BHQ (SEQ ID NO:12).

The same LONA assay is used to assay DNA purified from tail biopsies for mice derived from the targeted ES cells to determine their C5 genotypes and confirm that the humanized C5 allele has transmitted through the germ-line. Two pups heterozygous for the replacement are bred to generate a mouse that is homozygous for the replacement of the endogenous mouse C5 gene by the human C5 gene. Pups that are homozygous for the replacement are used for phenotyping.

The upstream junction of the murine locus and the sequence containing the human C5 gene is designed to be within 5'-TGAAAAACCT CCATTACTAC TTCTACAGAT GCCCACAGTG GTCTTGCATT CTATCCTTGT/(GC-GATCGC)/TCTGCCATCT CCTACTAGGC ATGTGGGGAA GGGGAATTCA GATGATGGTT GGAAATCTGG AAATTCTTTC CTCTCTTTTG TAATTTGCCT (SEQ ID NO:13), wherein the final mouse C5 nucleotide prior to the first nucleotide of the human C5 gene is the last T in CTTGT, and the first nucleotide of the human C5 sequence is the first T in TCTGC, which span the AsiSI site (within parentheses), wherein the precise junctions are indicated by forward slashes. The downstream junction of the sequence containing the human C5 gene and the fluxed neo selection cassette is designed to be within 5'-GCAAATAGGG CAGGCCACAG TGGCCTAATT AACCCACAAT GCAGCTGTCA AATATCAAAG AAGGTTTTGT GAATTAGCCT/CTCGAGATAA CTTCGTATAA TGTATGCTAT ACGAAGTTAT ATG-CATGGCC TCCGCGCCGG GTTTTGGCGC CTC-CCGCGGG (SEQ ID NO:14), wherein the final nucleotide of the human C5 sequence is the T in AGCCT, and the first nucleotide of the fluxed neo selection cassette is the first C in CTCGA, the precise junction being indicated by a forward slash. The downstream junction of the sequence of the murine C5 locus is designed to be within 5'-ATGTCTGGAA TAACTTCGTA TAATGTATGC TATACGAAGT TAT-GCTAGTA ACTATAACGG TCCTAAGGTA GCGAGCTAGC/CAGGCTATTA GGCTTCTGTC CCCAACTGTG GTGGCAAATA GGCCAGACCA CAGT-CACCAG ATGAAGCCAT AAATGCAGCT (SEQ ID NO:15), wherein the final nucleotide of the floxed neo selection cassette is the second C in CTAGC, and the first nucleotide of the murine C5 locus is the first C in CAGGC, the precise junction being indicated by a forward slash. The downstream junction of the sequence containing the human C5 gene and the murine locus is designed to be within 5'-GCAAATAGGG CAGGCCACAG TGGCCTAATT AACCCACAAT GCAGCTGTCA AATATCAAAG AAGGTTTTGT GAATTAGCCT/CTCGAG(ATAA CTTCGTATAA TGTATGCTAT ACGAAGTTAT) GCTAG-TAACT ATAACGGTCC TAAGGTAGCG AGCTAGC/CA GGCTATTAGG CTTCTGTCCC CAACTGTGGT GGCAAATAGG CCAGACCACA GTCACCAGAT GAAGCCATAA ATGCAGCTGA (SEQ ID NO:16), wherein the final nucleotide of the human C5 sequence is with the "T" in AGCCT, and the first nucleotide of the mouse C5 sequence is the first "C" in CAGGC; which span a loxP site (within parentheses) that remains after removal of the floxed neo selection cassette, wherein the precise junctions are indicated by forward slashes.

Example 2

Replacement of the Endogenous Mouse C3 Gene with a Human C3 Gene

Version 1—Replacement with Human C3 Promoter and Coding Exons 1 through 41

Figure 2A:
FIG. 2A provides an illustration, not to scale, of the mouse (mC3) and humanized (hC3) C3 genomic loci. The mouse C3 gene spanning the 5' regulatory elements and the coding region from exon 1 through exon 41 are deleted and replaced by the 5' regulatory elements and the coding region from exon 1 through exon 41 of the human C3 gene and a loxP site, as indicated by a bold line and an arrow, respectively.
Figure 2A:
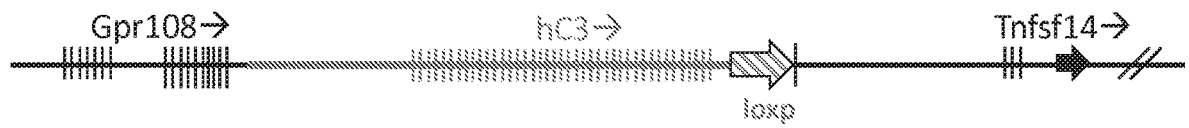

The human C3 gene containing 5' regulatory elements and all of the coding exons 1 through 41 of the human C3 gene replaced the murine C5 gene locus spanning 5' regulatory elements and all of the coding exons 2 through 41. The methods described above in Example 1 were basically used to replace the mouse C3 gene sequences with human C3 gene sequences. See FIG. 2A.

Preliminarily, a targeted deletion of 25 kb of the mouse C3 gene was generated in mouse ES cells by replacement of coding exons 2 through 41 and including 900 bp 3' to the polyadenylation site with a floxed neo cassette. The resultant mouse ES cells, 12132 ES cells, are a heterozygous C3 knockout. 12132 cells were used to generate C3 knockout mice according to procedures known in the art.

A targeting construct was generated containing mouse C3 upstream and downstream homology arms flanking a human C3 sequence extending from 5' regulatory elements upstream of coding exon 1 through coding exon 41 and the 3' untranslated region and a floxed hygro selection cassette, and electroporated into 12132 ES cells. Correctly targeted ES cells (MAID 6148) were further electroporated with a transient Cre-expressing vector to remove the drug selection cassette. Targeted ES cell clones without drug cassette (MAID 6149) were introduced into an 8-cell stage mouse embryo. F0 mice fully derived from the donor ES cell bearing the humanized C3 gene were identified by genotyping for loss of mouse allele and gain of human allele as described in Example 1.

Confirmation that the floxed neo cassette replaced the deleted mouse C3 gene sequence in the C3 knockout 12132 ES cells was confirmed by a TaqMan™ qPCR assay that comprises the following primer-probe sets (written 5' to 3'): 12132TU, mouse C3 intron 1: forward primer, GGCCT-GATTA CATGGACCTG TC (SEQ ID NO:17); reverse primer, CCCAGGCTTG GCTGGAATG (SEQ ID NO:18); probe, FAM-TGTCCACTCT GGAAGCCCAG GC-BHQ (SEQ ID NO:19); 12132TD, 3' of mouse C3 exon 41: forward primer, GCCAGGAGAG GAAGCTGGAG (SEQ ID NO:20); reverse primer, TGGCTCAGCA GTAAAGAACA C (SEQ ID NO:21); probe, FAM-ACA-GATTGCT GTGAGCTGCC CAAA-BHQ (SEQ ID NO:22); neo cassette: forward primer. GGTGGAGAGG CTATTCGGC (SEQ ID NO:23); reverse primer, GAACACGGCG GCATCAG (SEQ ID NO:24); probe, FAM-TGGGCACAAC AGACAATCGG CTG-BHQ (SEQ ID NO:25).

Confirmation that the human C3 gene sequence replaced the deleted mouse C3 gene sequence in the humanized allele was confirmed by a TaqMan™ qPCR assay that comprises the following primer-probe sets (written 5' to 3'): mC3-1, mouse C3 promoter: forward primer, GCCAGCCTAG CCTACTTCA (SEQ ID NO:26); reverse primer, GCCAC-CCATC CCAGTTCT (SEQ ID NO:27); probe, FAM-CA-GCCCAGGC CCTTTAGATT GCA-BHQ(SEQ ID NO:28); mC3-2, mouse C3 3' untranslated region, forward primer, TACGGTGTTA GGTTCACTAT TGGT (SEQ ID NO:29); reverse primer, GTCGCCAGCA GTCTCATACA G (SEQ ID NO:30); probe, CAL Orange-AGTGGGCATC CCTT-GCCAGG C-BHQ (SEQ ID NO:31); hygro cassette: forward primer, TGCGGCCGAT CTTAGCC (SEQ ID NO:32); reverse primer, TTGACCGATT CCTTGCGG (SEQ ID NO:33); probe, FAM-ACGAGCGGGT TCGGCCCATT C-BHQ (SEQ ID NO:34); hC3-1, human C3 promoter: forward primer, GGGCCTCCTA AGTTTGTTGA GTATC (SEQ ID NO:35); reverse primer, CAGGGCTGGT TCCCTAGAAA TC (SEQ ID NO:36); probe, FAM-TA-CAATAGCA GGCACAGCAC CCA-BHQ (SEQ ID NO:37); hC3-2, human C3 intron 1: forward primer, GGCT-GAGAGT GGGAGTCATG (SEQ ID NO:38); reverse primer, GCACTTGCCA ATGCCATTAT C (SEQ ID NO:39); probe, FAM-CTGCTGTCCT GCCCATGTGG TTG-BHQ (SEQ ID NO:40); hC3-3, human C3 exon 41: forward primer, CGAATGCCAA GACGAAGAGA AC (SEQ ID NO:41); reverse primer, GGGCACCCAA AGA-CAACCAT (SEQ ID NOA2); probe, CAL orange-CA-GAAACAAT GCCAGGACCT CGGC-BHQ (SEQ ID NO:43).

The same LONA assay is used to assay DNA purified from tail biopsies for mice derived from the targeted ES cells to determine their C3 genotypes and confirm that the humanized C3 allele had transmitted through the germ-line. Two pups heterozygous for the replacement are bred to generate a mouse that is homozygous for the replacement of the endogenous mouse C3 gene by the human C3 gene. Pups that are homozygous for the replacement are used for phenotyping.

The sequences of the junction of the murine C3 locus and the sequence containing the human C3 gene, the junction of the sequence containing the human C3 gene and the floxed hygro selection cassette, and the junction of the sequence of the floxed hygro selection cassette and the murine C3 locus are determined as described above in Example 1.

Version 2—Replacement with Human C3 Coding Exons 2 Through 41

Figure 2B:
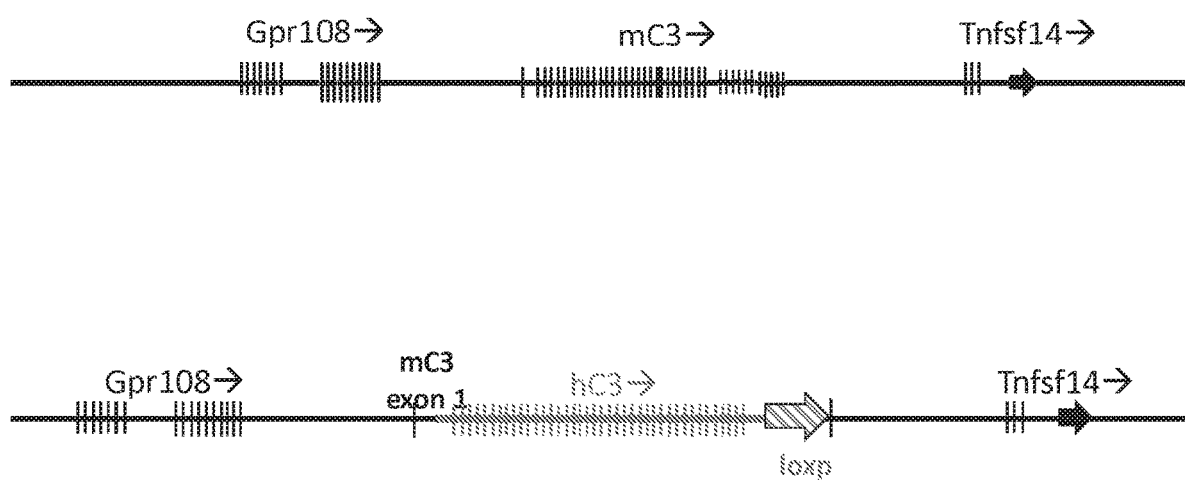
FIG. 2B provides an illustration, not to scale, of the mouse (mC3) and humanized (hC3) C3 genomic loci. The mouse C3 gene spanning a portion of intron 1 and the coding region from exon 2 through exon 41 are deleted and replaced by a portion of intron 1 and the coding region from exon 2 through exon 41 of the human C5 gene and a loxP site, as indicated by a bold line and an arrow, respectively.

The human C3 gene containing coding exons 2 through 41 of the human C3 gene replaced the murine C5 gene locus spanning coding exons 2 through 41. The methods described above in Example 1 were basically used to replace the mouse C3 gene sequences with human C3 gene sequences. See FIG. 2B.

Preliminarily, a targeted deletion of 25 kb of the mouse C3 gene was generated in mouse ES cells by replacement of coding exons 2 through 41 and including 900 bp 3' to the polyadenylation site with a floxed neo cassette. The resultant mouse ES cells, 12132 ES cells, are a heterozygous C3 knockout.

A targeting construct was generated containing mouse C3 upstream and downstream homology arms flanking a human C3 sequence extending from upstream of coding exon 2 through coding exon 41 and the 3' untranslated region and a floxed hygro selection cassette, and electroporated into 12132 ES cells. Correctly targeted ES cells (MAID 6155) were further electroporated with a transient Cre-expressing vector to remove the drug selection cassette. Targeted ES cell clones without drug cassette (MAID 6156) were introduced into an 8-cell stage mouse embryo. F0 mice fully derived from the donor ES cell bearing the humanized C3 gene were identified by genotyping for loss of mouse allele and gain of human allele as described in Example 1.

Confirmation that the floxed neo cassette replaced the deleted mouse C3 gene sequence in the C3 knockout 12132 ES cells, and that the human C3 gene sequence replaced the deleted mouse C3 gene sequence in the humanized allele, was confirmed by a TaqMan™ qPCR assay that comprises the same primer-probe sets (written 5' to 3') as described above in Version 1.

The same LONA assay is used to assay DNA purified from tail biopsies for mice derived from the targeted ES cells to determine their C3 genotypes and confirm that the humanized C3 allele had transmitted through the germ-line. Two pups heterozygous for the replacement are bred to generate a mouse that is homozygous for the replacement of the endogenous mouse C3 gene by the human C3 gene. Pups that are homozygous for the replacement are used for phenotyping.

The sequences of the junction of the murine C3 locus and the sequence containing the human C3 gene, the junction of the sequence containing the human C3 gene and the floxed hygro selection cassette, and the junction of the sequence of the floxed hygro selection cassette and the murine C3 locus are determined as described above in Example 1.

Example 3

Complement Hemolytic Activity Assay in Mouse Serum

Complement has been implicated in ocular inflammatory and retinal degenerative diseases (see Mullins et al, (2000) Drusen associated with aging and age-related macular degeneration contain proteins common to extracellular deposits associated with atherosclerosis, elastosis, amyloidosis, and dense deposit disease, *FASEB J*, 14(7):835-846). Blocking C5 cleavage by monoclonal antibody (mAb) is a possible therapeutic strategy for these disorders (see Copland et al. (2009) Systemic and local anti-C5 therapy reduces the disease severity in experimental autoimmune uveoretinitis, *Clinical and Experimental Immunology*, 159:303-314). For evaluation of therapies directed at complement, such as C5 and/or C3 antagonists, assays are necessary to evaluate the function of candidate therapeutics in vitro and in vivo in appropriate models of human diseases, disorders and conditions associated with complement activation.

Methods

Complement hemolytic activity was assessed using Classical Complement Assay $CH_{50}$ (Gilcas et al. (2001) Classical pathway evaluation, *Current Protocols in Immunology*, Unit 13.1). Mouse blood was collected from the heart and clotted in eppendorf tubes on ice for 1 hour: serum was separated by centrifugation and stored at −70° C. Sheep erythrocytes (E) were sensitized by incubation with rabbit anti-sheep hemolysin for 20 min at 37° C. Sensitized cells ($E_A$) were incubated for 1 hour at 37° C. with doubling dilutions of treated or control serum from mouse or human. Intact $E_A$ cells were pelleted and supernatant was removed to measure absorbance at 541 nm, an index of hemolysis. $E_A$ cells incubated with buffer only (0% lysis) or with $ddH_2O$ (100% lysis) served as negative and positive controls respectively. Percentage of hemolysis and $CH_{50}$ in each well were calculated relative to the $ddH_2O$ control (Holt et al. (2001) Targeted deletion of the CD59 gene causes spontaneous intravascular hemolysis and hemoglobinuria, *Blood*, 98(2): 442-449). Mice, including $C5^{hu/hu}$, $C5^{-/-}$, $C3^{hu/hu}$, $C3^{-/-}$, and respective control strains, were generated with Velocigene® technology as described in Examples 1 and 2. Normal, C5-depleted, and C3-depleted human sera were obtained from Quidel Corp., and used as controls or for comparison. Complement components were added to test if the hemolysis function can be restored. Tested sera were incubated for 40 min at 4° C. with complement components; human C5 (Sigma-Aldrich or Quidel Corp., 50 µg/ml), human C3 (Sigma-Aldrich or Quidel Corp., 10, 400, 1200 µg/ml) and murine C5 (Regeneron Pharmaceuticals, 50 µg/ml). Anti-human C5 mAb (100 µg/ml) and anti-mouse C5 mAb (Hycult Biotech, 10 µg/ml) were used to confirm the specificity and utility of this system for future drug discovery.

Results

Figure 3:
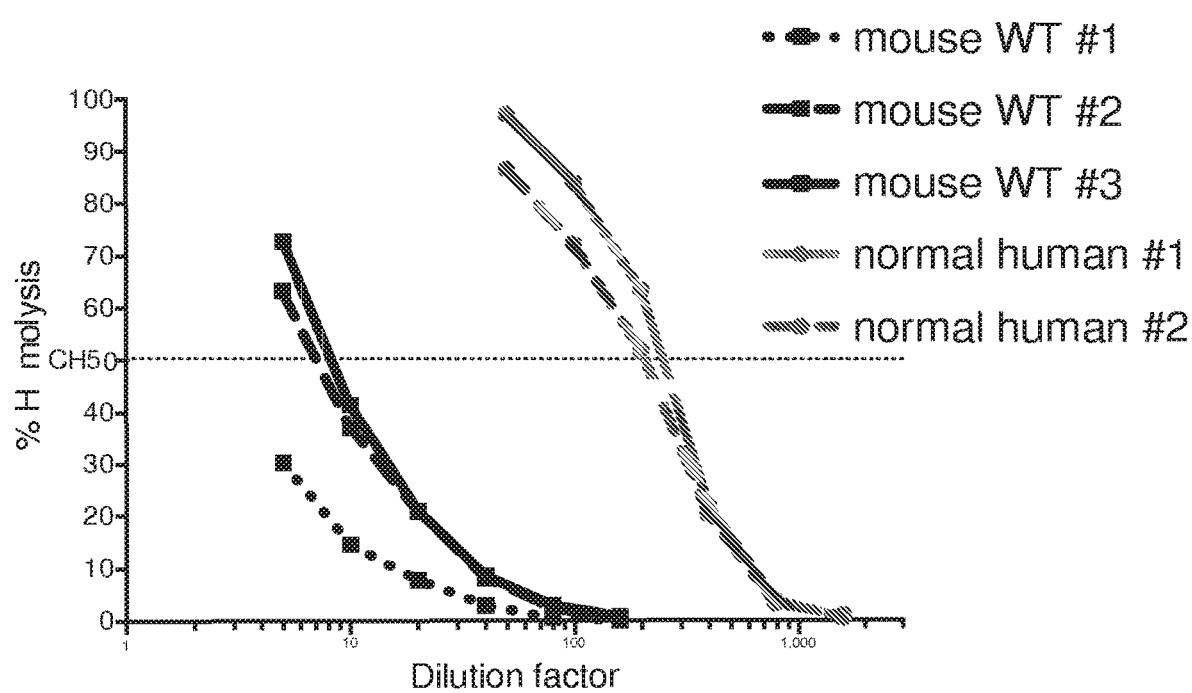
FIG. 3 shows that mouse complement has lower activity in a hemolytic assay than human complement.

Wild-type mouse sera have approximately 10 times lower complement hemolytic activity compared to normal human sera. As shown in FIG. 3, the complement hemolytic activity, as determined using the $CH_{50}$ value, was at least 10 times lower in three lots of normal or wild-type mouse sera as compared to two lots of human sera.

Figure 4:
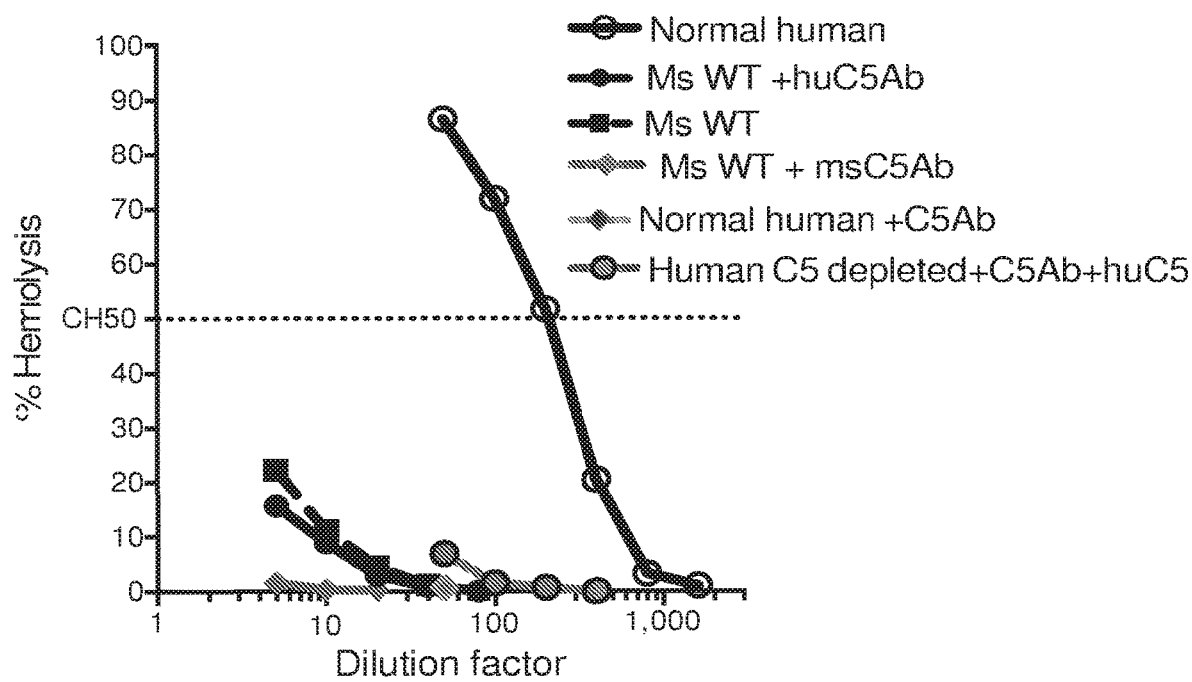
FIG. 4 shows that complement hemolytic activity is blocked by species-specific anti-C5 monoclonal antibodies in a species-specific manner.

Anti-C5 monoclonal antibodies block hemolysis in a species-specific manner. As shown in FIG. 4, an anti-mouse C5 monoclonal antibody (msC5Ab) blocked complement hemolytic activity in normal mouse serum, and an anti-human C5 mAb (C5Ab) blocked hemolytic activity in normal human serum and human C5-depleted serum supplemented with human C5 protein, but not in normal mouse serum.

Figure 5A:
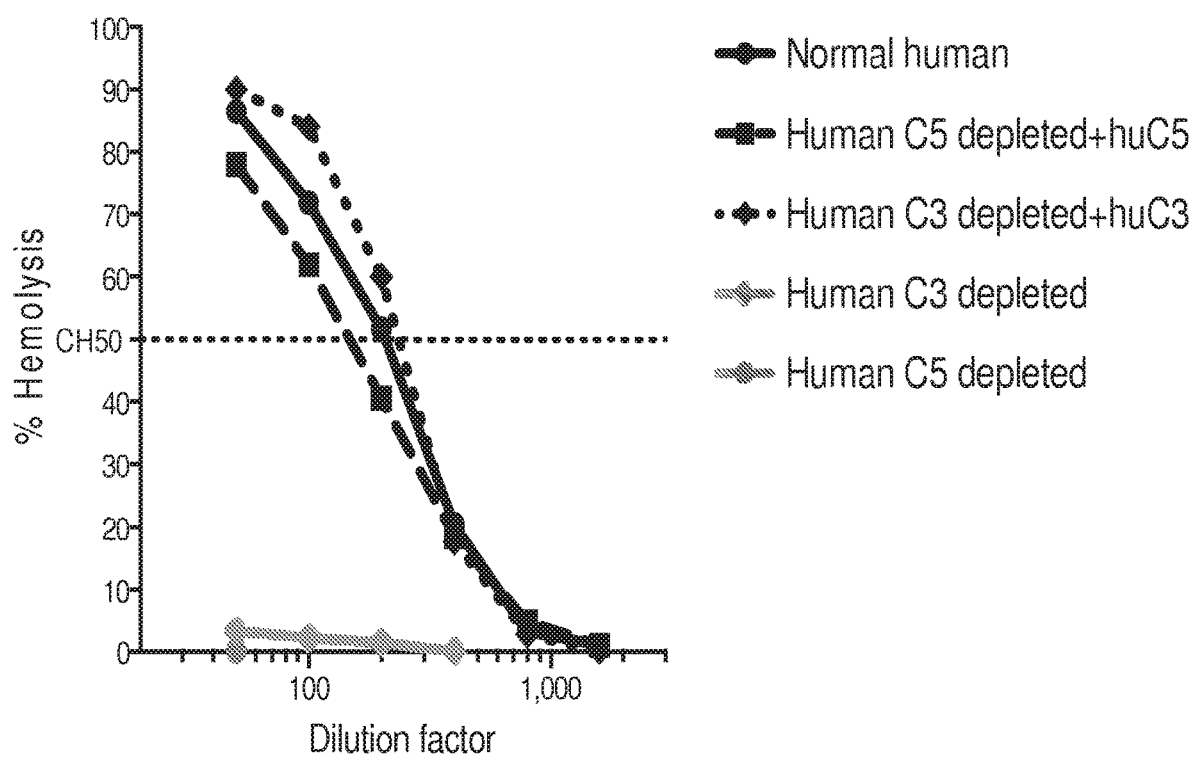
FIG. 5A and FIG. 5B depict graphs showing that humanized C5 mice are functional mouse C5 knockouts. Addition of human C5 or C3 protein reconstitutes hemolytic activity in C5 or C3-depleted human serum, respectively, as depicted in FIG. 5A. Mouse, but not human, C5 protein reconstitutes hemolytic activity in C5$^{-/-}$ and humanized C5 mouse sera, depicted in FIG. 5B.

Human C5 and C3 proteins display species-specific hemolytic activity. As shown in FIG. 5A, human C5 and C3 proteins were able to reconstitute complement hemolytic activity of human C5- and C3-depleted human serum, respectively.

Figure 5B:
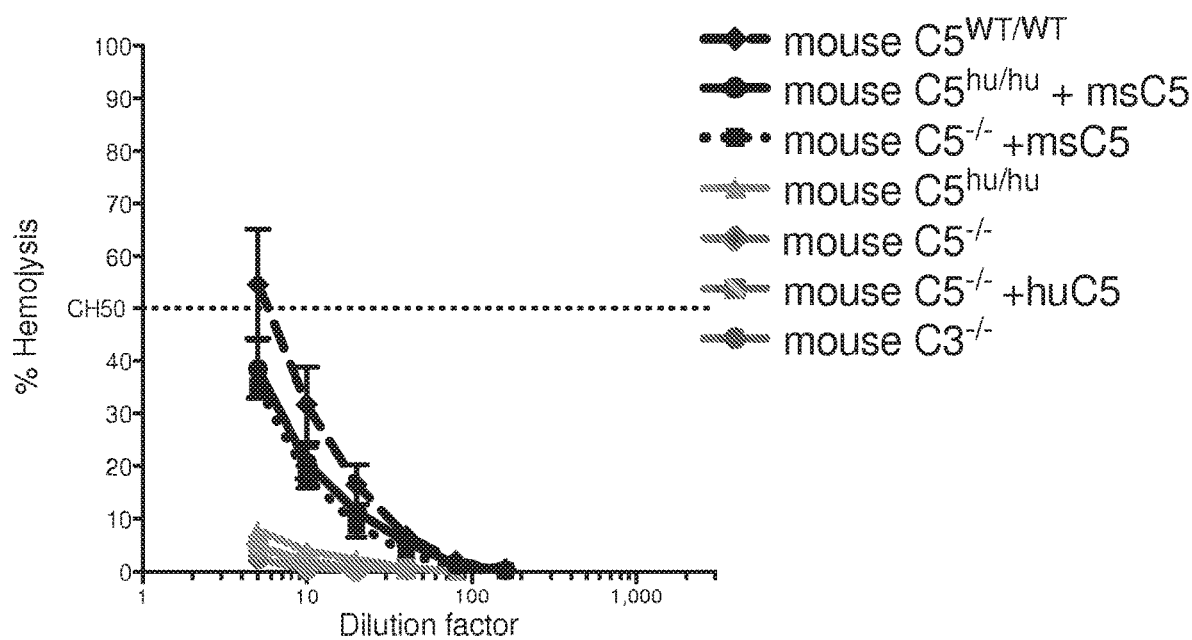

As shown in FIG. 5B, sera from $C5^{-/-}$ and $C3^{-/-}$ mice showed a lack of complement activity, and humanized $C5^{hu/hu}$ mouse serum displayed no hemolytic activity, essentially equivalent to serum from $C5^{-/-}$ and $C3^{-/-}$ mice. The addition of mouse C5 protein to humanized $C5^{hu/hu}$ mouse serum rescued complement hemolytic activity, but addition of human C5 protein to humanized $C5^{hu/hu}$ mouse serum did not rescue complement activity.

Figure 5C:
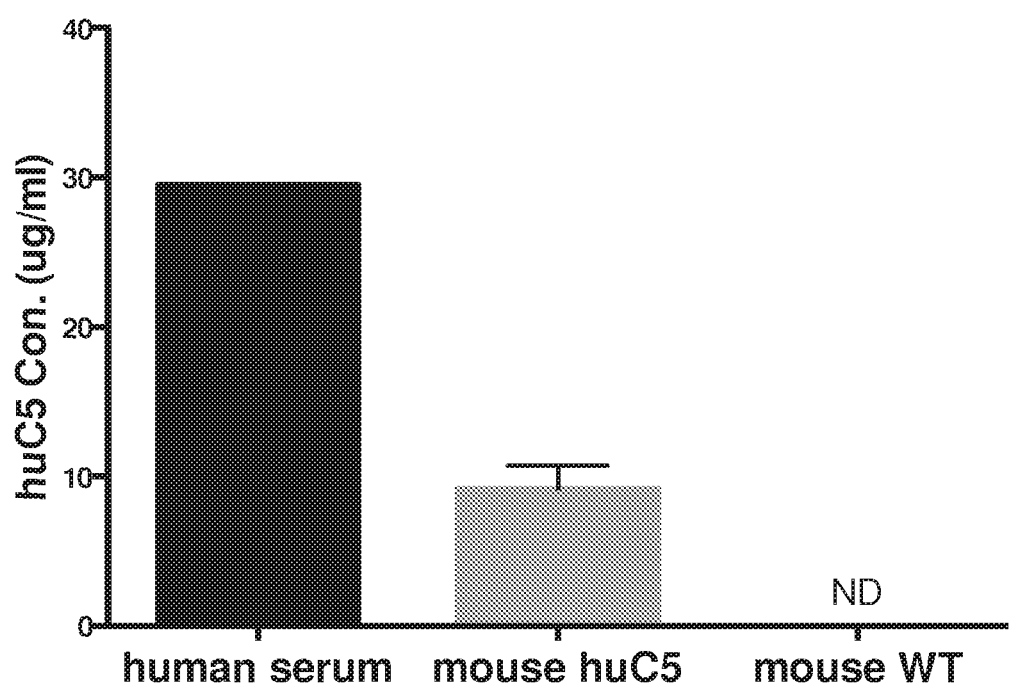
FIG. 5C is a bar graph depicting levels of human C5 protein in humanized C5 mouse serum that are three times lower than in human serum.
Figure 5D:
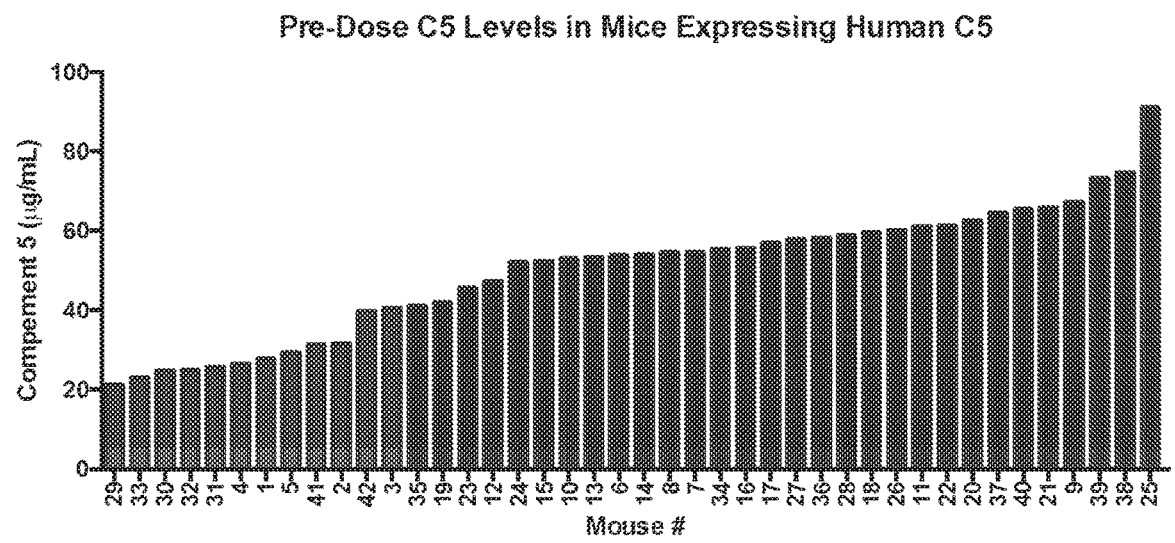
FIG. 5D is a bar graph depicting that pre-dose complement C5 levels in humanized C5 mice vary between males and females. A range of human C5, from 20-100 µg/mL is present in humanized C5 mouse serum.

As shown in FIG. 5C, the lack of complement hemolytic activity of humanized $C5^{hu/hu}$ mouse serum appears not to be due to a lack of human C5 protein, as the amount of human C5 protein present in the serum of these mice was about one third the amount of C5 protein present in normal human serum. FIG. 5D shows the variation between male and female humanized C5 mice with respect to pre-dose complement C5 levels. The range of human C5 protein present in the serum of these mice ranged from 20 to 100 µg/ml, which was sufficient to show hemolytic activity in serum. Human C5 normally added in these experiments was 50 µg/ml.

Figure 6:
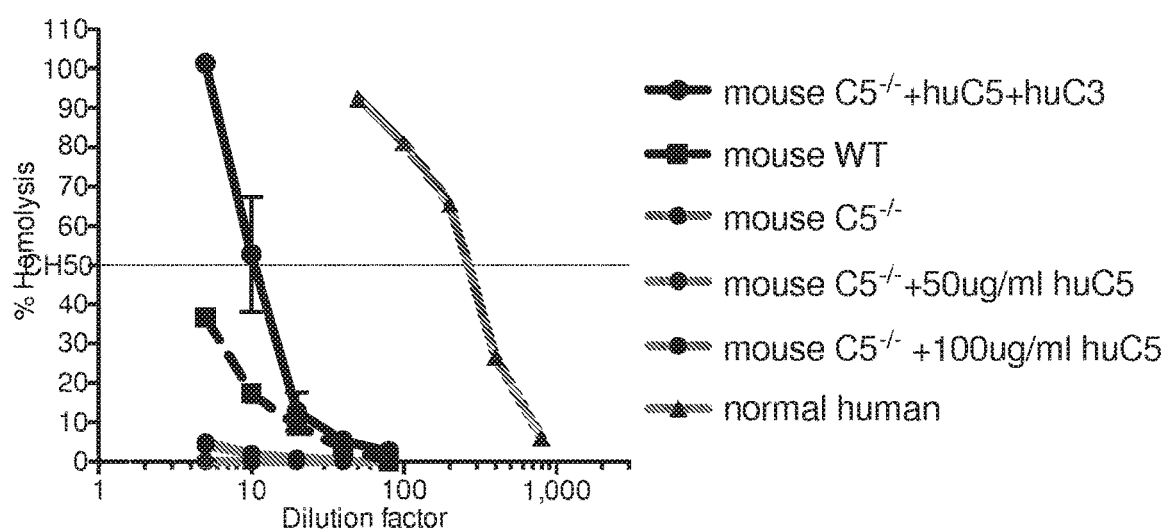
FIG. 6 shows that addition of human C3 and C5 proteins, but not human C5 protein alone, reconstitutes hemolytic activity in C5$^{-/-}$ mouse serum.

Both human C5 and C3 proteins are required to reconstitute hemolytic activity in mouse C5 knockout sera. As shown in FIG. 6, complement hemolytic activity could not be recovered by adding human C5 protein to C5$^{-/-}$ mouse serum, whereas the addition of human C3 and C5 proteins together rescued hemolysis in C5$^{-/-}$ mouse serum.

Figure 7:
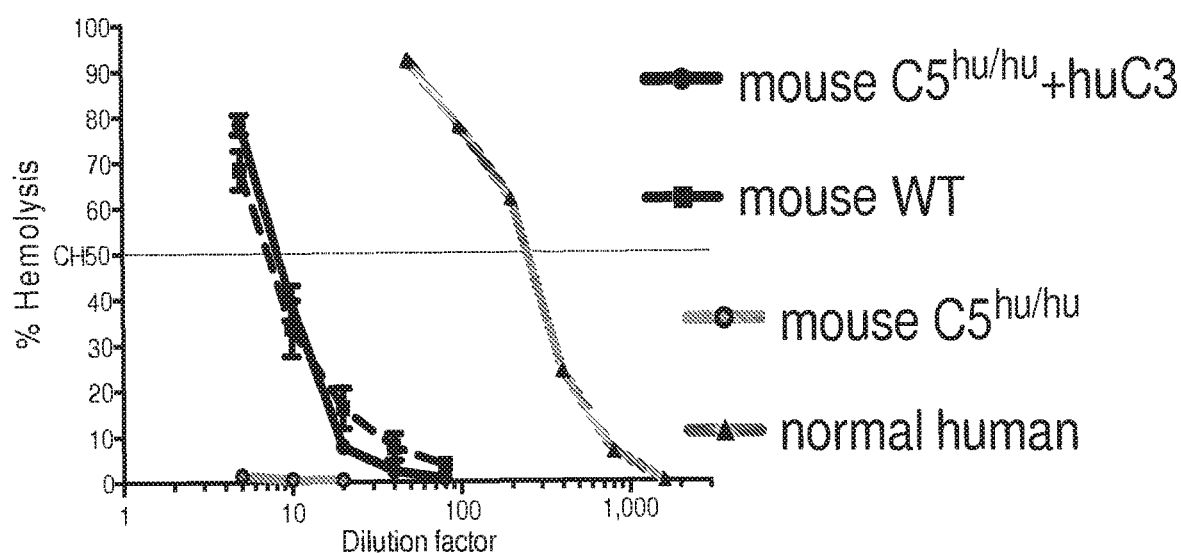
FIG. 7 shows that humanized C5 mouse serum requires addition of human C3 protein to achieve wild-type levels of mouse hemolytic activity.
Figure 8A:
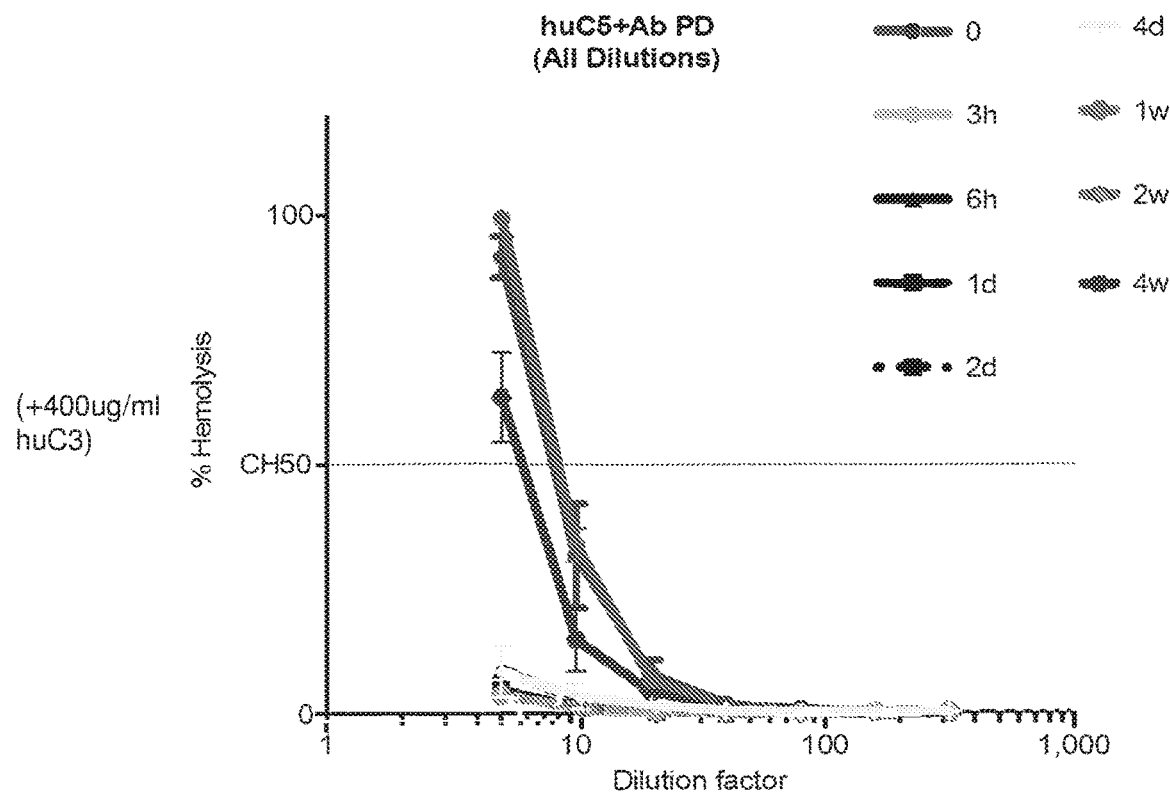
FIG. 8A depicts graphs showing the results of a hemolysis assay performed on serum samples from humanized C5 mice exposed to the anti-human C5 antibody (C5Ab) using 400 µg/mL human C3 protein.
Figure 8A:
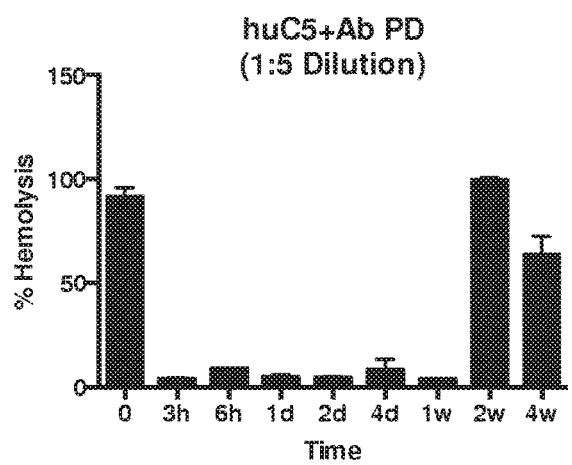
Figure 8B:
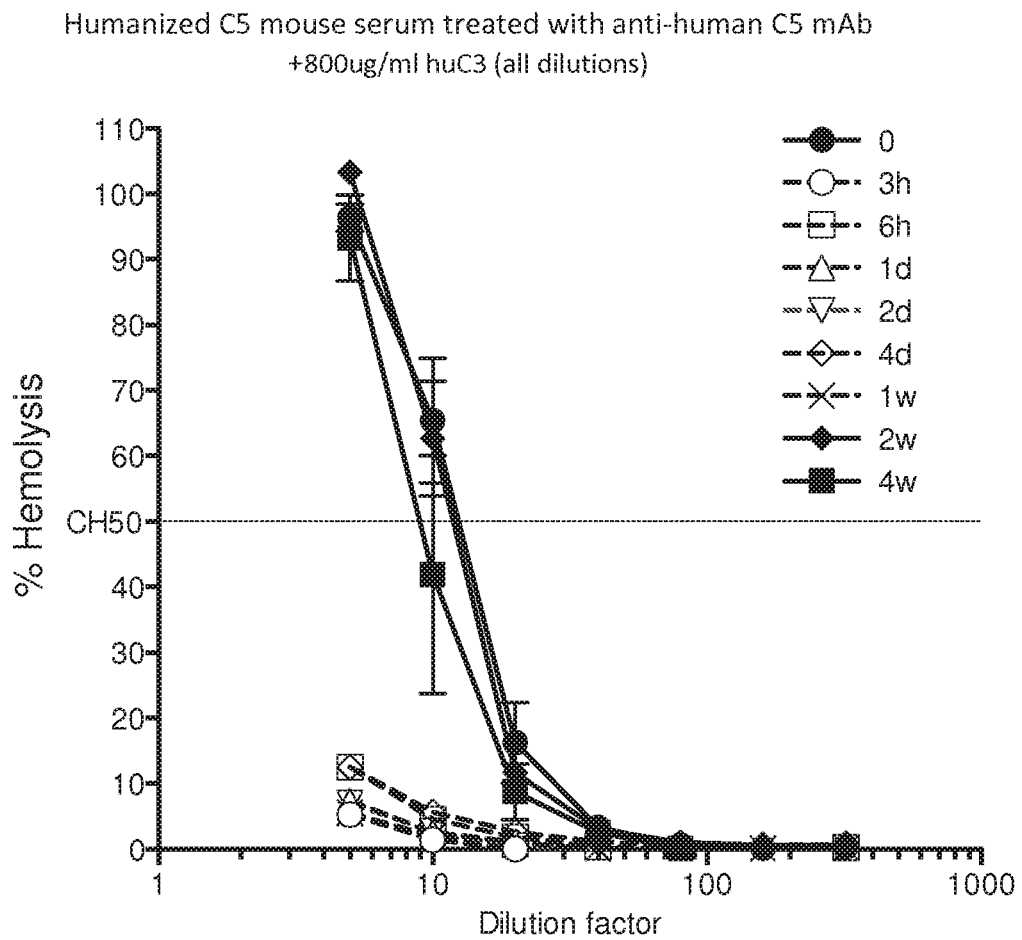
FIG. 8B depicts graphs showing the results of a hemolysis assay performed on serum samples from humanized C5 mice exposed to the anti-human C5 antibody (C5Ab) using 800 µg/mL human C3 protein.
Figure 8B:
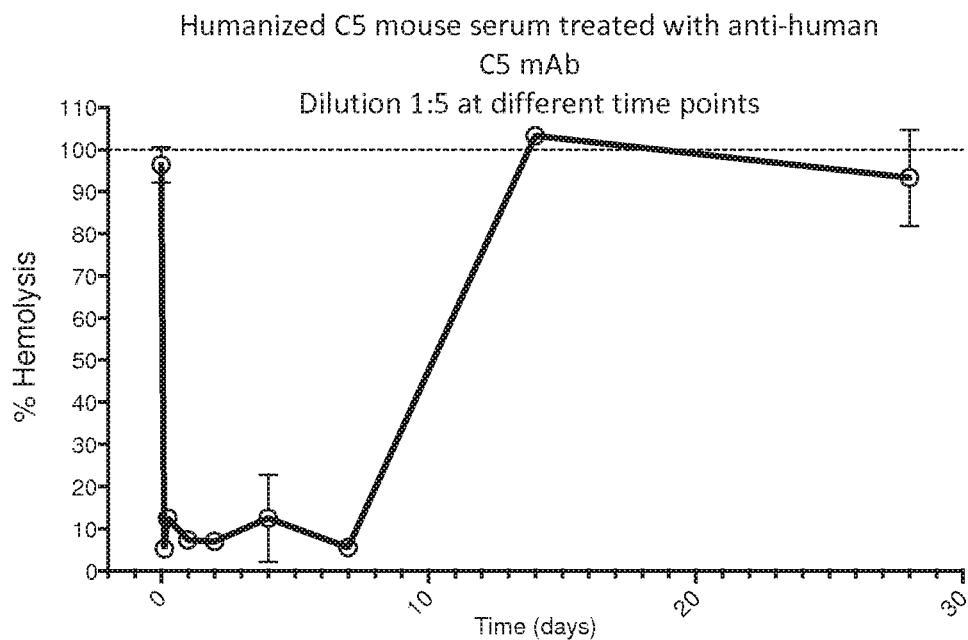

Addition of human C3 protein rescues hemolytic activity in C5$^{hu/hu}$ mouse serum. As shown in FIG. 7, human C3 protein is sufficient to reconstitute complement hemolytic activity in serum from C5$^{hu/hu}$ mice.

Based on the above results, humanized C5$^{hu/hu}$ and/or C3$^{hu/hu}$ mice are appropriate non-human animals to evaluate the PK and PD of human-specific C5 and/or C3 antagonists. Based on the above results, doubly humanized C5$^{hu/hu}$ and C3$^{hu/hu}$ mouse serum may display complement hemolytic activity without a requirement for supplementation by human C5 and/or C3 proteins, thereby constituting an appropriate mouse strain for in vivo testing of the therapeutic efficacy of human-specific C5 and/or C3 antagonists.

Conclusions

Wild-type mouse serum has dramatically lower complement hemolytic activity compared to human serum. Genetically modified mice expressing human C5 are functional murine C5 knockouts, possibly because mouse convertase cannot cleave human C5 protein. Humanized C5 mouse serum needs the addition of human C3 protein to achieve wild-type levels of complement hemolytic activity.

Example 4

Uses for Humanized C5 and/or C3 Mice

Humanized C5 and/or C3 mice are useful to evaluate the pharmacodynamics (PD) of human-specific C5 and/or C3 compounds (such as, antagonists, e.g., neutralizing anti-C5 or anti-C3 antibodies).

Pharmacokinetics (PK) and PD assays in humanized C5 and/or C3 mice are performed according to standard procedures known in the art, for example, as described in U.S. Pat. No. 6,355,245 for an anti-C5 antibody.

Humanized C5 and/or C3 mice are useful to test the in vivo therapeutic efficacy of human-specific C5 or C3 antagonists, e.g., neutralizing anti-C5 or anti-C3 antibodies, in a variety of disease models, for example and not for limitation: dry age-related macular degeneration (AMD); wet AMD; experimental autoimmune uveoretinitis (EAU); ocular hypertension; and optic nerve injury. (See, e.g., Makrides (1998) and Molines et al. (2006) for a list of diseases, disorders and conditions associated with complement activation).

Dry AMD can be induced in humanized C5 and/or C3 mice by high fat diet and blue light damage (see, e.g., *Exp Eye Res,* 2002, 75(5):543-553), cigarette smoke (see, e.g., *Invest Ophthalmol Vis Sci.* 2006, 47(2):729-737), carboxyethylpyrrole (CEP) (see, e.g., *Invest. Ophthalmol. Vis. Sci.* 2010, 51:1276-1281; Nat Med. 2012, 18(5):791-798).

The humanized C5 and/or C3 mice can also be bred to other transgenic AMD models, such as, for example, ApoE (−/−)(see, e.g., *Invest. Ophthalmol, Vis. Sci.* 2000, 41:2035-2042), Mdm1 (see, e.g., *Hum. Mol. Genet.* 2008, 17:3929-3941), Sod1 (−/−)(see, e.g., *PNAS* 2006; 103:11282-11287), LDLR(−/−)(see, e.g., *Br J Ophthalmol* 2005, 89:1627-1630), and DICER1 (−/−) (see, e.g., *Nature.* 2011; 471 (7338):325-330).

Wet AMD can be induced in humanized C5 and/or C3 mice by laser-induced choroidal neovascularization (CNV) (see *Nat Protoc.* 2013, 8(11):2197-2211).

EAU can be induced in humanized C5 and/or C3 mice (see, e.g., *Clin Exp Immunol.* 2010, 159(3): 303-314).

Ocular hypertension can be induced in humanized C5 and/or C3 mice (see, e.g., *Experimental Eye Research* 2006, 83:620-628).

Optic nerve injury can be induced in humanized C5 and/or C3 mice (see, e.g., *J Neurotrauma* 2003, 20(9):895-904.

Humanized C5 mice can be used to evaluate human-specific C5 antagonists in a variety of disease models, for example and not for limitation: paroxysmal nocturnal hematuria; neuromyletic optica; renal transplantation; and kidney injury. (See, e.g., U.S. Pat. No. 6,355,245.)

Therapeutic efficacy assays using humanized C5 and/or C3 mice are performed according to standard procedures known in the art, for example, as described in U.S. Pat. No. 6,355,245 for an anti-C5 antibody.

Example 5

Pharmacokinetic/Pharmacodynamic Study of an Anti-C5 Antibody in Humanized C5 Homozygous Mice This example utilizes male and female humanized C5 homozygous mice prepared according to the prior Examples to test the ability of an anti-C5 antibody to decrease complement activation.

Methods

A total of 25 C5$^{hu/hu}$ mice (males and females) were used in the study. Serum (20 µL) was collected from two mice at each designated timepoint, which included a "predose" timepoint as well as timepoints at 3 h, 6 h, 1 d, 2 d, 4 d, 1 W, 2 W, 4 W following subcutaneous administration of 15 mg/kg of an anti-human C5 monoclonal antibody. Samples were stored at −20° C. until assayed for pharmacokinetics (PK) and pharmacodynamics (PD) alteration of complement activation.

Complement hemolytic activity was assessed as described above in Example 3. As above, human C3 (Sigma-Aldrich or Quidel Corp., 400 and 800 µg/ml) was added to serum to recapitulate the human complement system.

Results

As shown in FIG. 8, subcutaneous injection of 15 mg/kg of an anti-human C5 antibody decreases complement activation for at least one week post injection. This effect was observed irrespective of whether 400 µg/ml (FIG. 8A) or 800 µg/ml (FIG. 8B) human C3 protein was added to the hemolytic assays.

Figure 9A:
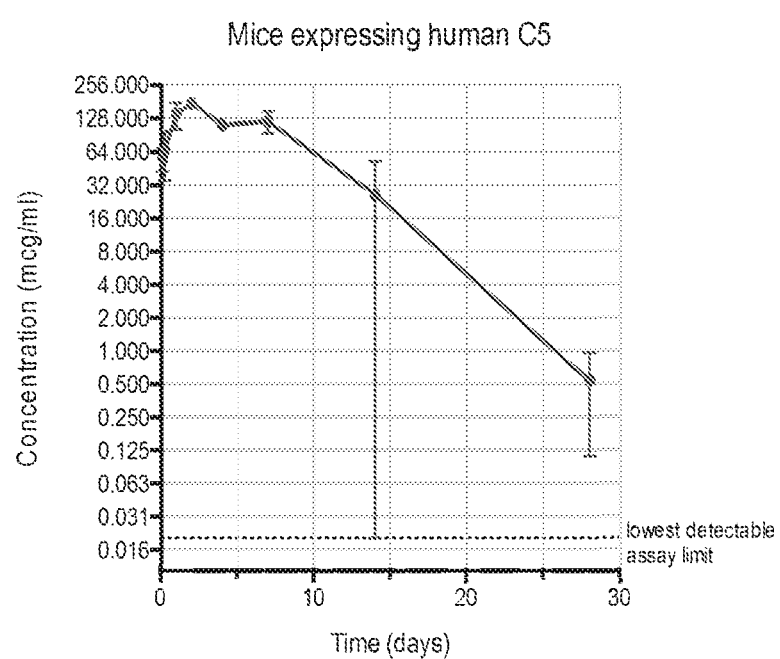
FIG. 9A depicts a graph showing the results of a pharmacokinetic assay measuring anti-human C5 antibody levels as a function of time post-injection for all animals in the study.
Figure 9B:
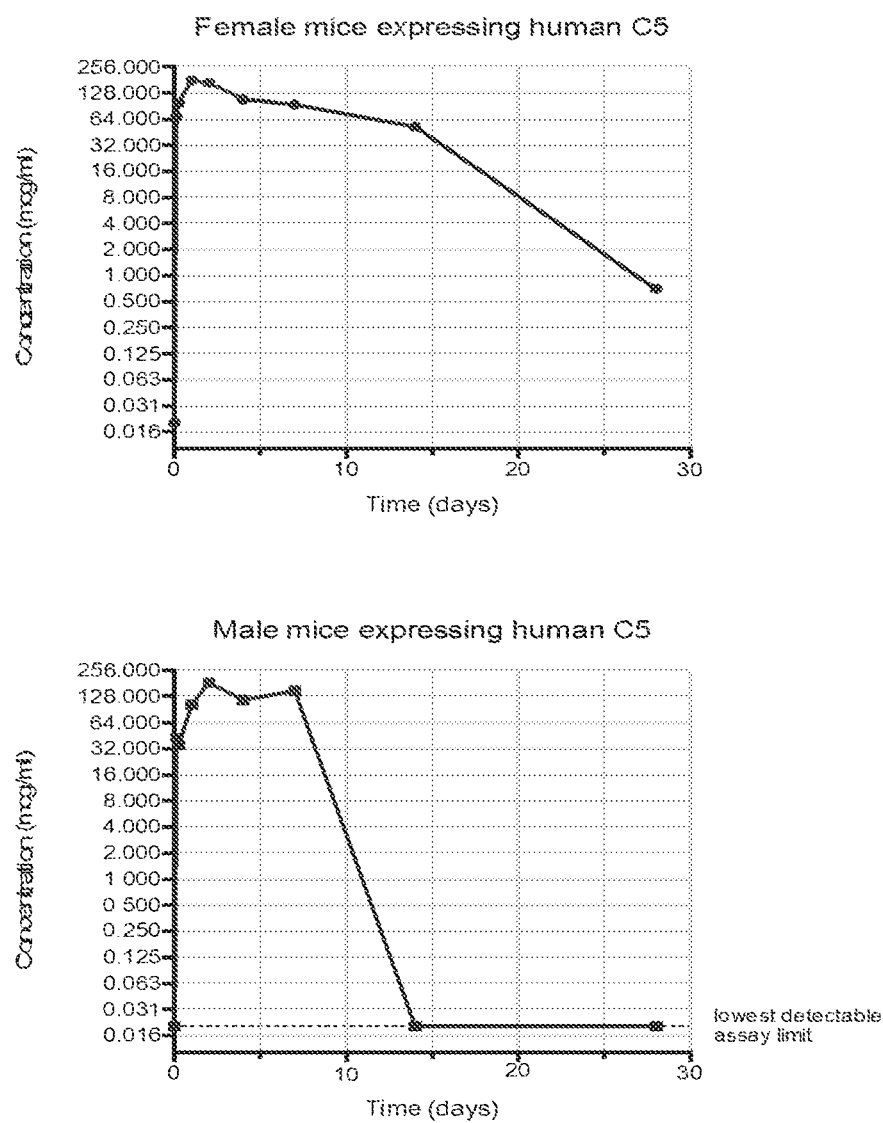
FIG. 9B depicts graphs showing the results of a pharmacokinetic assay measuring anti-human C5 antibody levels as a function of time post-injection for female (top) and male (bottom) animals.

As shown in FIG. 9, PK analysis of C5 monoclonal antibody revealed clearance over time of this antibody with 2 out of 5 mice having undetectable levels by day 28.

Example 6

Cross Activity of Human and Mouse Complement Proteins

This Example investigated the cross-activity of human and mouse C3 and C5 proteins using the engineered mice described in the previous examples. As discussed in Example 3 and as shown in FIG. 6, the human C5 and the mouse C3 proteins are not sufficient to reconstitute hemolytic activity in mice lacking endogenous C5. In this study, the ability of mouse C5 and human C3 to restore hemolytic activity in C3 knockout mice was observed, Methods Complement hemolytic activity was assessed as described in Example 3.

Mice, including C5$^{-/-}$, C3$^{-/-}$", and respective control strains, were generated with Velocigene® technology as described in Examples 1 and 2. Normal, C3-depleted human sera were obtained from Quidel Corp. and used as controls or for comparison. Complement components were added to test if the hemolysis function can be restored. Tested sera were incubated for 40 min at 4° C. with complement components; human C3 (Sigma-Aldrich or Quidel Corp., 50, 100, 500, 1200 µg/ml); and human C5 (Sigma-Aldrich or Quidel Corp., 50 µg/ml),). Anti-human C5 mAb (100 µg/ml) and anti-mouse C5 mAb (Hycult Biotech, 10 µg/ml) were used to confirm the specificity and utility of this system for future drug discovery.

Results

Figure 10A:
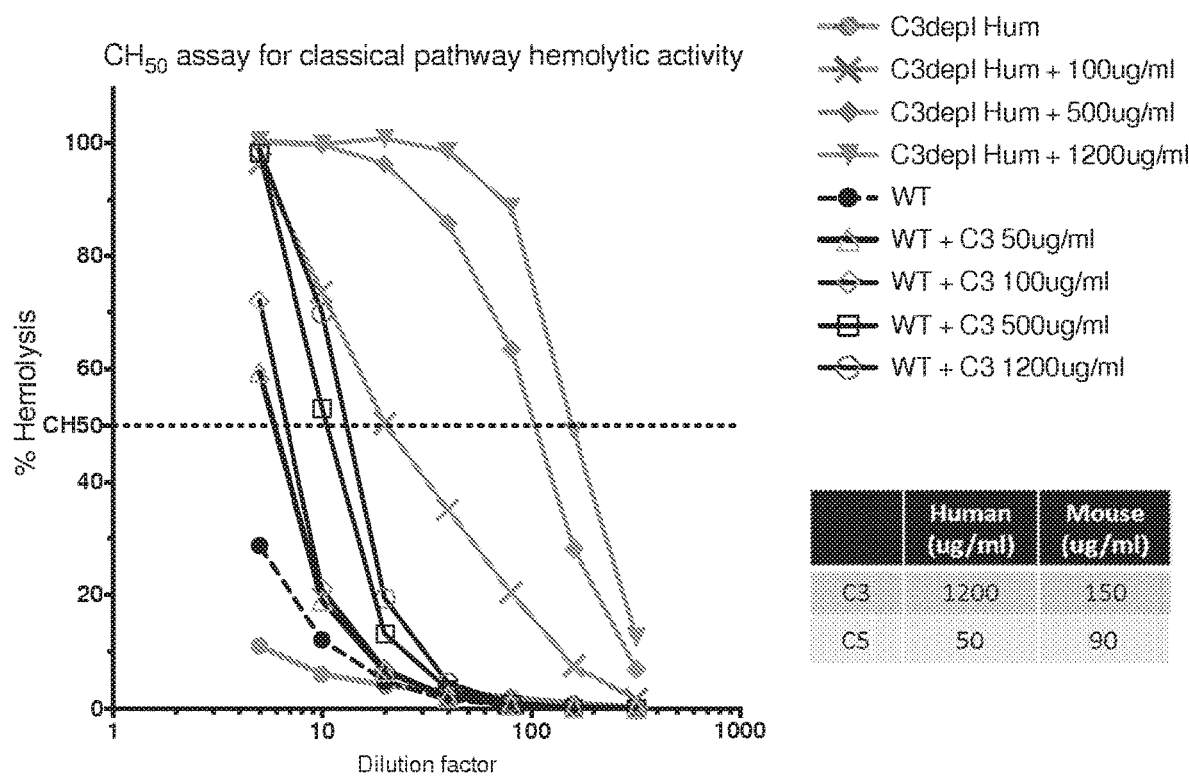
FIG. 10A shows that adding human C3 protein to wild type mouse serum can enhance hemolytic function but not to the same extent observed in normal human serum (for each data point from mice, serum was mixed from 3 animals).
Figure 10B:
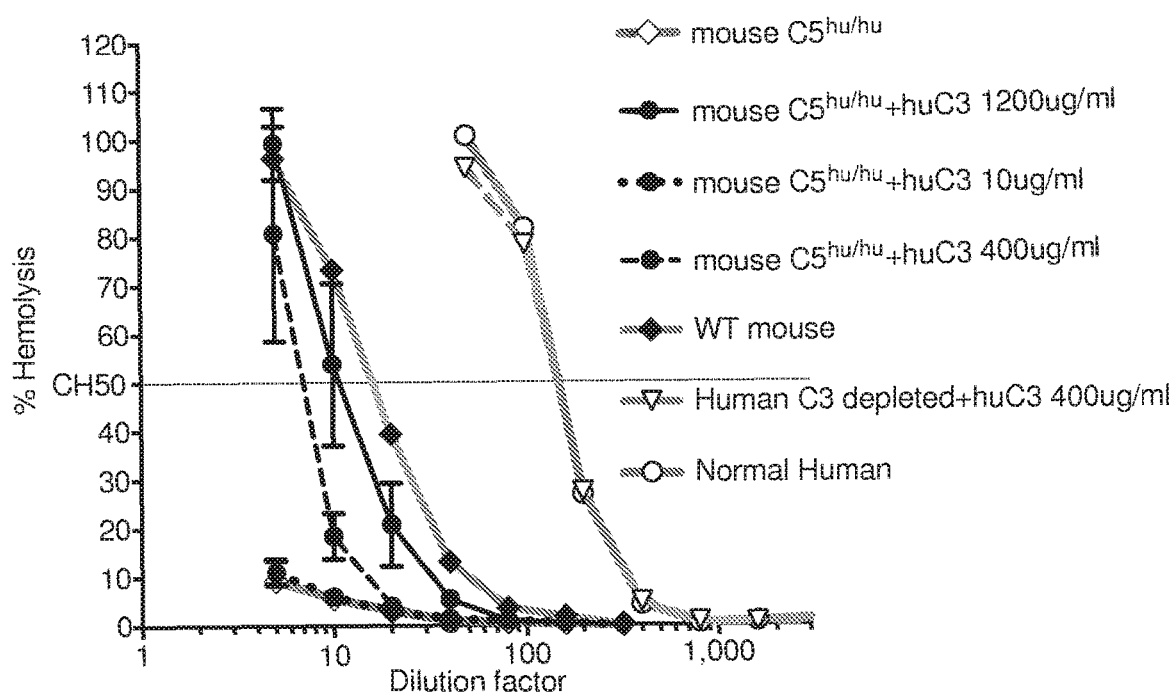
FIG. 10B shows that hemolytic function can be restored in humanized C5$^{hu/hu}$ mice when supplemented with human C3 protein.

As shown in FIG. 10A, addition of human C3 protein to wild type mice serum can enhance hemolytic function over that observed in wild type controls. However, when compared to the addition of human C3 protein back into C3-depleted human serum, the observed enhancement is less than that shown in humans. Further, as illustrated in FIG. 10B, percentage hemoloysis is restored using humanized C5$^{hu/hu}$ mouse serum supplemented with human C3 protein.

Figure 11:
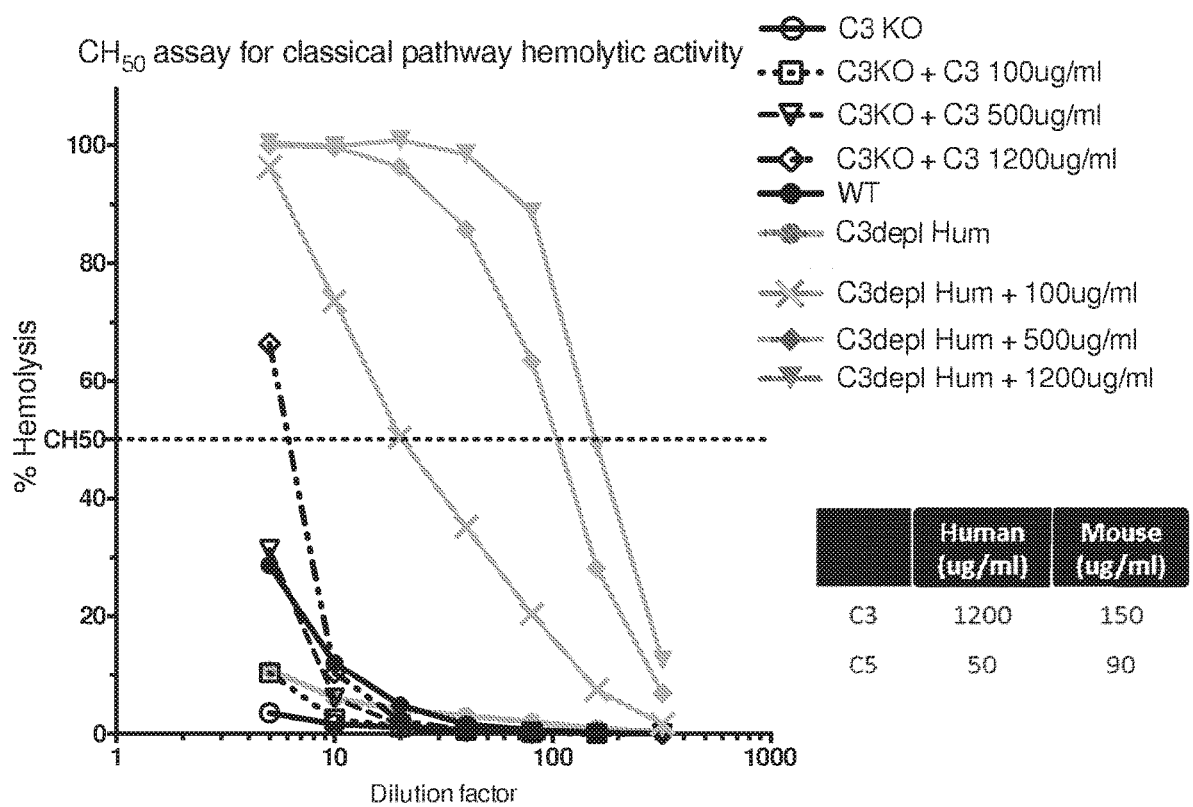
FIG. 11 shows that adding human C3 protein to serum derived from C3 knockout mice can rescue hemolytic function (for each data point from mice, serum was mixed from 3 animals).

When this experiment was repeated using sera derived from C3 knockout animals, it was shown that adding human C3 protein to C3$^{-/-}$ serum rescues hemolytic function, particularly with increasing concentrations of added human C3 (FIG. 11).

Figure 12:
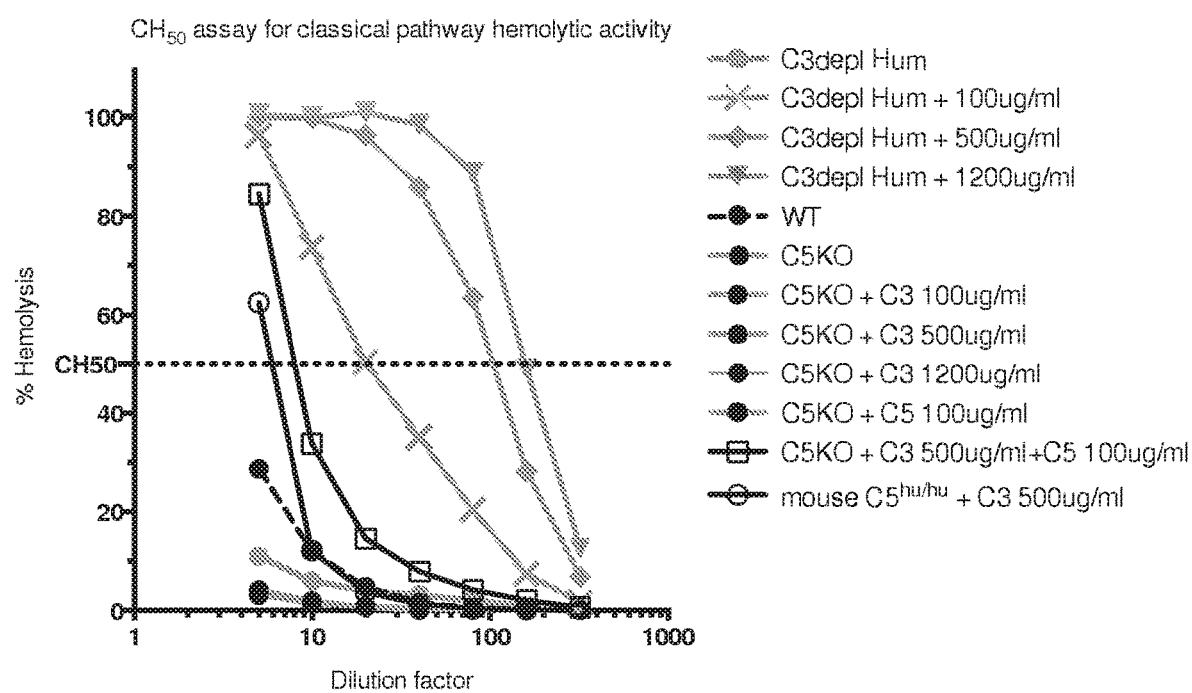
FIG. 12 shows that adding human C3 protein only to C5 knockout mouse serum cannot rescue hemolytic function (for each data point from mice, serum was mixed from 3 animals).

In contrast, FIG. 12 shows that addition of human C3 to C5 null animal-derived sera does not rescue hemolytic function.

Conclusions

In summary, the data derived from the present example demonstrates that while human C3 is able to cross-react with murine C5, mouse C3 is similarly unable to cross-react with human C5 to recapitulate complement activity in vitro. A summary of these results is presented below in Table 1.

TABLE 1

Summary of mouse and human C3, C5 cross-activity

| Mouse | +human | Classical pathway Complement activity |
|---|---|---|
| WT | C3 | >WT |
| WT | C5 | |
| WT | C3, C5 | |
| C3KO | C3 | =WT |
| C3KO | C5 | |
| C3KO | C3, C5 | =WT |
| C5KO | C3 | 0 |
| C5KO | C5 | 0 |
| C5KO | C3, C5 | ≥WT |

What is claimed is:

1. A rodent whose genome comprises a replacement of a rodent C3 gene sequence at an endogenous rodent C3 locus with a human C3 gene sequence to form a modified C3 gene, wherein the rodent C3 gene sequence comprises an exon of the endogenous rodent C3 gene and the human C3 gene sequence comprises exon 2 through exon 41 of the human C3 gene, and wherein the rodent is a mouse or a rat.

2. The rodent of claim 1, wherein the rodent is a rat.

3. The rodent of claim 1, wherein the rodent is a mouse.

4. The rodent of claim 1, wherein the rodent is a rat, and wherein expression of the modified C3 gene is under control of rodent regulatory elements at the endogenous rodent C3 locus.

5. The rodent of claim 1, wherein the rodent is a mouse and the modified C3 gene comprises exon 1 of the endogenous mouse C3 gene and exon 2 through exon 41 of the human C3 gene, and wherein expression of the modified C3 gene is under control of rodent regulatory elements at the endogenous rodent C3 locus.

6. The rodent of claim 1, wherein the human C3 gene sequence comprises exon 1 through exon 41 of the human C3 gene.

7. The rodent of claim 6, wherein the rodent is a rat.

8. The rodent of claim 6, wherein the rodent is a mouse.

9. The rodent of claim 1, wherein the rodent is a mouse that is incapable of expressing a mouse C3 protein.

10. The rodent of claim 1, wherein the rodent is a mouse that expresses a mouse C5 protein encoded by an endogenous mouse C5 gene.

11. The rodent of claim 1, wherein the mouse expresses a human or humanized C5 protein.

12. The rodent of claim 11, wherein the genome of the mouse comprises a replacement of a mouse C5 gene sequence at an endogenous mouse C5 locus with a human C5 gene sequence to form a modified C5 gene, and wherein the modified C5 gene encodes the human or humanized C5 protein.

13. The rodent of claim 12, wherein expression of the modified C5 gene is under control of mouse regulatory elements at the endogenous mouse C5 locus.

14. The rodent of claim 1, wherein the rodent is a mouse that expresses human C3 protein in serum at a concentration of at least about 10% of the level of mouse C3 protein present in the serum of an age-matched mouse that expresses functional endogenous mouse C3 protein, but does not comprise the replacement.

15. The rodent of claim 1, wherein the rodent is a mouse that expresses human C3 protein in serum at a concentration of:

(a) between about 100 μg/ml and about 1500 μg/ml; or (b) at least about 100 μg/ml.

16. A method for making a humanized rodent, comprising replacing a rodent C3 gene sequence at an endogenous rodent C3 locus with a human C3 gene sequence to form a modified C3 gene, wherein the human C3 gene sequence comprises exon 2 through exon 41 of the human C3 gene, and wherein the rodent is a mouse or a rat.

17. The method of claim 16, wherein the rodent is a rat.

18. The method of claim 16, wherein the rodent is a mouse.

19. The method of claim 16, wherein expression of the modified C3 gene is under control of rodent regulatory elements at the endogenous rodent C3 locus.

20. The method of claim 19, wherein the rodent is a rat.

21. The method of claim 19, wherein the rodent is a mouse and the modified C3 gene comprises exon 1 of the endogenous mouse C3 gene and exon 2 through exon 41 of the human C3 gene.

22. The method of claim 16, wherein the human C3 gene sequence comprises exon 1 through exon 41 of the human C3 gene.

23. The method of claim 22, wherein the rodent is a rat.

24. The method of claim 22, wherein the rodent is a mouse.

* * * * *

SEQUENCE LISTING

```
<160> NUMBER OF SEQ ID NOS: 43

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
cctccggtta actggtttgt gat                                              23

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gcagtgaatg gtagacttcc ca                                               22

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
agtgacttta ctttggttgt tctgctcaca                                       30

<210> SEQ ID NO 4
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 4
ccgggaaagg aaaccaagac                                               20

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
cagcacagac tgaggatcca a                                             21

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
agactgtcat tctggcccgg acct                                          24

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
tgctcttaaa ggaccatcat cac                                           23

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
gtaaacggat aacggaaagg ataga                                         25

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
ccatttccaa atgcacttcc cagc                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
cccactgaac tatcacagga aaca                                          24

```
<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
ggagatgcat tccagtctct gtta                                              24

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
tgaagatgac ctccggatgt aacgg                                             25

<210> SEQ ID NO 13
<211> LENGTH: 158
<212> TYPE: DNA
<213> ORGANISM: Artificial Sequence
<220> FEATURE:
<223> OTHER INFORMATION: Synthetic oligonucleotide

<400> SEQUENCE: 13
tgaaaaacct ccattactac ttctacagat gcccacagtg gtcttgcatt ctatccttgt       60
gcgatcgctc tgccatctcc tactaggcat gtggggaagg ggaattcaga tgatggttgg      120
aaatctggaa attctttcct ctcttttgta atttgcct                              158

<210> SEQ ID NO 14
<211> LENGTH: 160
<212> TYPE: DNA
<213> ORGANISM: Artificial Sequence
<220> FEATURE:
<223> OTHER INFORMATION: Synthetic oligonucleotide

<400> SEQUENCE: 14
gcaaataggg caggccacag tggcctaatt aacccacaat gcagctgtca aatatcaaag       60
aaggttttgt gaattagcct ctcgagataa cttcgtataa tgtatgctat acgaagttat      120
atgcatggcc tccgcgccgg gttttggcgc ctcccgcggg                            160

<210> SEQ ID NO 15
<211> LENGTH: 160
<212> TYPE: DNA
<213> ORGANISM: Artificial Sequence
<220> FEATURE:
<223> OTHER INFORMATION: Synthetic oligonucleotide

<400> SEQUENCE: 15
atgtctggaa taacttcgta taatgtatgc tatacgaagt tatgctagta actataacgg       60
tcctaaggta gcgagctagc caggctatta ggcttctgtc cccaactgtg gtggcaaata      120
ggccagacca cagtcaccag atgaagccat aaatgcagct                            160

<210> SEQ ID NO 16
<211> LENGTH: 239
<212> TYPE: DNA
<213> ORGANISM: Artificial Sequence
<220> FEATURE:
<223> OTHER INFORMATION: Synthetic oligonucleotide
```

<400> SEQUENCE: 16
gcaaataggg caggccacag tggcctaatt aacccacaat gcagctgtca aatatcaaag    60
aaggttttgt gaattagcct ctcgagataa cttcgtataa tgtatgctat acgaagttat   120
gctagtaact ataacggtcc taaggtagcg agctagccag gctattaggc ttctgtcccc   180
aactgtggtg gcaaataggc cagaccacag tcaccagatg aagccataaa tgcagctga    239

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ggcctgatta catggacctg tc                                             22

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
cccaggcttg gctggaatg                                                 19

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 19
tgtccactct ggaagcccag gc                                             22

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gccaggagag gaagctggag                                                20

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
tggctcagca gtaaagaaca c                                              21

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
acagattgct gtgagctgcc caaa                                             24

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
ggtggagagg ctattcggc                                                   19

<210> SEQ ID NO 24
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 24
gaacacggcg gcatcag                                                     17

<210> SEQ ID NO 25
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 25
tgggcacaac agacaatcgg ctg                                              23

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26
gccagcctag cctacttca                                                   19

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
gccacccatc ccagttct                                                    18

<210> SEQ ID NO 28
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 28
cagcccaggc cctttagatt gca                                              23

<210> SEQ ID NO 29
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 29
tacggtgtta ggttcactat tggt                                       24

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
gtcgccagca gtctcataca g                                          21

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
agtgggcatc ccttgccagg c                                          21

<210> SEQ ID NO 32
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 32
tgcggccgat cttagcc                                               17

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33
ttgaccgatt ccttgcgg                                              18

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
acgagcgggt tcggcccatt c                                          21

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
gggcctccta agtttgttga gtatc                                      25
```

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 36
cagggctggt tccctagaaa tc                                              22

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
tacaatagca ggcacagcac cca                                             23

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ggctgagagt gggagtcatg                                                 20

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
gcacttgcca atgccattat c                                               21

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
ctgctgtcct gcccatgtgg ttg                                             23

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
cgaatgccaa gacgaagaga ac                                              22

<210> SEQ ID NO 42
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 42
gggcacccaa agacaaccat                                                    20

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
cagaaacaat gccaggacct cggc                                               24
```